US008377897B2

(12) United States Patent
Teng et al.

(10) Patent No.: US 8,377,897 B2
(45) Date of Patent: Feb. 19, 2013

(54) COMPOSITIONS AND METHODS FOR NON-PARENTERAL DELIVERY OF OLIGONUCLEOTIDES

(75) Inventors: Ching-Leou Teng, San Diego, CA (US); Phillip Dan Cook, Lake San Marcos, CA (US); Lloyd Tillman, Carlsbad, CA (US); Gregory E. Hardee, Rancho Sante Fe, CA (US); David J. Ecker, Encinitas, CA (US); Muthiah Manoharan, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/237,063

(22) Filed: Sep. 28, 2005

(65) Prior Publication Data
US 2007/0249551 A1 Oct. 25, 2007

Related U.S. Application Data

(63) Continuation of application No. 09/315,298, filed on May 20, 1999, now abandoned, which is a continuation-in-part of application No. 09/108,673, filed on Jul. 1, 1998, now Pat. No. 6,887,906, which is a continuation-in-part of application No. 08/886,829, filed on Jul. 1, 1997, now abandoned.

(51) Int. Cl.
A61K 31/70 (2006.01)
C07H 21/02 (2006.01)
C07H 21/04 (2006.01)

(52) U.S. Cl. ..................... 514/44 A; 536/24.5
(58) Field of Classification Search ........................ None
See application file for complete search history.

(56) References Cited

U.S. PATENT DOCUMENTS

| | | |
|---|---|---|
| 3,687,808 A | 8/1972 | Merigan et al. |
| 4,052,986 A * | 10/1977 | Scaife ............................ 604/204 |
| 4,469,863 A | 9/1984 | Ts'o et al. |
| 4,476,301 A | 10/1984 | Imbach et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,689,320 A | 8/1987 | Kaji |
| 4,762,779 A | 8/1988 | Snitman |
| 4,789,737 A | 12/1988 | Miyoshi et al. |
| 4,806,463 A | 2/1989 | Goodchild et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yammane et al. |
| 4,878,979 A | 11/1989 | Steinbach |
| 4,904,582 A | 2/1990 | Tullis |
| 4,948,882 A | 8/1990 | Ruth |
| 4,958,013 A | 9/1990 | Letsinger |
| 4,981,957 A | 1/1991 | Lebleu et al. |
| 5,004,810 A | 4/1991 | Draper |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,087,617 A | 2/1992 | Smith |
| 5,098,890 A | 3/1992 | Gewirtz et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,135,917 A | 8/1992 | Burch |
| 5,138,045 A | 8/1992 | Cook et al. |
| 5,149,797 A | 9/1992 | Pederson et al. |
| 5,166,195 A | 11/1992 | Ecker |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,428 A | 3/1993 | Agrawal et al. |
| 5,212,295 A | 5/1993 | Cook |
| 5,214,134 A | 5/1993 | Weis et al. |

(Continued)

FOREIGN PATENT DOCUMENTS

| | | |
|---|---|---|
| CA | 218654 | 7/1997 |
| CA | 2294988 | 7/1998 |

(Continued)

OTHER PUBLICATIONS

Curone et al. (see p. 777); European Society of Gastrointestinal and Abdominal Radiology (ESGAR) 8th Annual Meeting and Postgraduate Course: Clinical Gastrointestinal and Abdominal Radiology: Update for the 2000's. Eur. Radlol. 7,771-809 (1997).* Moolenaar et al. (International Journal of Pharmaceutics, 1995—vol. 114:117-120).*
Akamo et al., "Chemotherapy Targetig Regional Lymph Nodes by Gastric Submucosal Injection of Liposomal Adriamycin in Patients with Gastric Carcinoma" Jpn. J. Cancer Res. (1994) 85:652-658.
Albert et al., "Antisense knockouts: molecular scalpels for the dissection of signal transduction" Trends in Pharmacological Sciences (1994) 15:250-254.
Aungst et al., "Site Dependence of Absorption-Promoting Actions of Laureth-9 Na Salicylate, Na2EDTA, and Aprotinin on Rectal, Nasal, and Buccal Insulin Delivery" Pharm. Res. (1988) 5:305-308.

(Continued)

Primary Examiner — Terra Cotta Gibbs
(74) Attorney, Agent, or Firm — Knobbe Martens

(57) ABSTRACT

The present invention relates to compositions and methods which enhance the local and systemic uptake and delivery of oligonucleotides and nucleic acids via non-parenteral routes of administration. Pharmaceutical compositions comprising oligonucleotides disclosed herein include, for systemic delivery, emulsion and microemulsion formulations for a variety of applications and oral dosage formulations. It has also surprisingly been discovered that oligonucleotides may be locally delivered to colonic sites by rectal enemas and suppositories in simple solutions, e.g., neat or in saline. Such pharmaceutical compositions of oligonucleotides may further include one or more penetration enhancers for the transport of oligonucleotides and other nucleic acids across mucosal membranes. The compositions and methods of the invention are utilized to effect the oral, buccal, rectal or vaginal administration of an antisense oligonucleotide to an animal in order to modulate the expression of a gene in the animal for investigative, therapeutic, palliative or prophylactic purposes.

9 Claims, No Drawings

U.S. PATENT DOCUMENTS

| | | |
|---|---|---|
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,223,168 A | 6/1993 | Holt |
| 5,223,618 A | 6/1993 | Cook et al. |
| 5,235,033 A | 8/1993 | Summerton et al. |
| 5,242,906 A | 9/1993 | Pagano et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,298,614 A | 3/1994 | Yano et al. |
| 5,317,098 A | 5/1994 | Shizuya et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush et al. |
| 5,378,825 A | 1/1995 | Cook et al. |
| 5,386,023 A | 1/1995 | Sanghvi et al. |
| 5,391,723 A | 2/1995 | Priest |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,455,335 A | 10/1995 | Kahne et al. |
| 5,457,187 A | 10/1995 | Gmeiner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,506,351 A | 4/1996 | McGee |
| 5,508,270 A | 4/1996 | Baxter et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,514,788 A | 5/1996 | Bennett et al. |
| 5,519,126 A | 5/1996 | Hecht |
| 5,519,134 A | 5/1996 | Acevedo et al. |
| 5,521,302 A | 5/1996 | Cook |
| 5,523,389 A | 6/1996 | Ecker et al. |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,539,083 A | 7/1996 | Cook et al. |
| 5,541,306 A | 7/1996 | Agrawal et al. |
| 5,541,307 A | 7/1996 | Cook et al. |
| 5,541,313 A | 7/1996 | Ruth |
| 5,543,508 A | 8/1996 | Haseloff et al. |
| 5,545,729 A | 8/1996 | Goodchild et al. |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,554,746 A | 9/1996 | Ravikumar et al. |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,567,811 A | 10/1996 | Misiura et al. |
| 5,571,799 A | 11/1996 | Tkachuk et al. |
| 5,571,902 A | 11/1996 | Ravikumar et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,587,470 A | 12/1996 | Cook et al. |
| 5,591,584 A | 1/1997 | Chang et al. |
| 5,591,623 A | 1/1997 | Bennett et al. |
| 5,591,721 A | 1/1997 | Agrawal et al. |
| 5,591,722 A | 1/1997 | Montgomery et al. |
| 5,591,840 A | 1/1997 | Narayanan et al. |
| 5,594,121 A | 1/1997 | Froehler et al. |
| 5,595,726 A | 1/1997 | Magda et al. |
| 5,595,978 A | 1/1997 | Draper et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,797 A | 2/1997 | Cook et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,631,237 A | 5/1997 | Dzau et al. |
| 5,633,360 A | 5/1997 | Bischofberger et al. |
| 5,639,873 A | 6/1997 | Barascut et al. |
| 5,641,754 A * | 6/1997 | Iversen ..................... 514/44 A |
| 5,646,265 A | 7/1997 | McGee |
| 5,652,355 A | 7/1997 | Metelev et al. |
| 5,652,356 A | 7/1997 | Agrawal |
| 5,656,272 A | 8/1997 | Le et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,359 A | 9/1997 | Digenis et al. |
| 5,674,530 A | 10/1997 | Amidon et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,697,248 A | 12/1997 | Brown |
| 5,700,920 A | 12/1997 | Altmann et al. |
| 5,700,922 A | 12/1997 | Cook |
| 5,705,188 A | 1/1998 | Junichi et al. |
| 5,707,648 A | 1/1998 | Yiv |
| 5,714,331 A | 2/1998 | Buchardt et al. |
| 5,716,780 A | 2/1998 | Edwards et al. |
| 5,719,262 A | 2/1998 | Buchardt et al. |
| 5,780,444 A | 7/1998 | Kahne |
| 5,801,154 A | 9/1998 | Baracchini et al. |
| 5,843,738 A * | 12/1998 | Bennett et al. ................. 435/375 |
| 5,846,525 A | 12/1998 | Maniar et al. |
| 5,853,748 A | 12/1998 | New et al. |

| | | | |
|---|---|---|---|
| 5,859,221 A | 1/1999 | Cook et al. | |
| 5,877,162 A | 3/1999 | Werner et al. | |
| 5,877,309 A * | 3/1999 | McKay et al. | 536/24.5 |
| 5,948,898 A | 9/1999 | Dean et al. | |
| 5,955,059 A | 9/1999 | Gilchrest et al. | |
| 5,955,589 A | 9/1999 | Cook | |
| 5,980,861 A | 11/1999 | Hnatowich et al. | |
| 5,994,062 A | 11/1999 | Mulshine | |
| 6,008,048 A | 12/1999 | Monia et al. | |
| 6,037,176 A | 3/2000 | Bennett et al. | |
| 6,080,580 A | 6/2000 | Baker et al. | |
| 6,096,722 A * | 8/2000 | Bennett et al. | 514/44 |
| 6,111,094 A | 8/2000 | Bennett et al. | |
| 6,120,803 A | 9/2000 | Wong et al. | |
| 6,127,533 A | 10/2000 | Cook et al. | |
| 6,133,031 A | 10/2000 | Monia et al. | |
| 6,159,694 A | 12/2000 | Karras | |
| 6,200,602 B1 * | 3/2001 | Watts et al. | 424/463 |
| 6,228,642 B1 | 5/2001 | Baker et al. | |
| 6,262,241 B1 | 7/2001 | Cook et al. | |
| 6,335,434 B1 | 1/2002 | Guzaev et al. | |
| 6,528,631 B1 | 3/2003 | Cook et al. | |
| 6,582,908 B2 | 6/2003 | Fodor et al. | |
| 6,610,674 B1 * | 8/2003 | Schreiber | 514/177 |
| 6,727,064 B2 | 4/2004 | Karras | |
| 6,747,014 B2 * | 6/2004 | Teng et al. | 514/44 |
| 6,841,539 B1 | 1/2005 | Mehta et al. | |
| 6,887,906 B1 | 5/2005 | Teng et al. | |
| 7,341,741 B1 | 3/2008 | Sachetto et al. | |
| 2001/0053519 A1 | 12/2001 | Fodor et al. | |
| 2003/0228597 A1 | 12/2003 | Cowsert et al. | |
| 2007/0249551 A1 | 10/2007 | Teng et al. | |

FOREIGN PATENT DOCUMENTS

| | | | |
|---|---|---|---|
| EP | 1017404 B1 * | 9/1998 | |
| JP | 57080314 | 5/1982 | |
| JP | 07330614 | 12/1995 | |
| JP | 07330614 A | 12/1995 | |
| WO | WO 92/20823 | 11/1992 | |
| WO | WO 92/21353 | 12/1992 | |
| WO | WO 93/19660 | 10/1993 | |
| WO | WO 93/24510 | 12/1993 | |
| WO | WO 94/00155 | 1/1994 | |
| WO | WO 94/02499 | 2/1994 | |
| WO | WO 94/05333 | * 3/1994 | |
| WO | WO 94/17093 | 8/1994 | |
| WO | WO 94/18835 | 9/1994 | |
| WO | WO 95/11748 | 5/1995 | |
| WO | WO 95/14037 | 5/1995 | |
| WO | WO 9514037 A1 | 5/1995 | |
| WO | WO 96/12497 | 5/1996 | |
| WO | WO 96/30051 | 10/1996 | |
| WO | WO 96/32496 | 10/1996 | |
| WO | WO 96/34008 | 10/1996 | |
| WO | WO 96/40081 | 12/1996 | |
| WO | WO 96/41011 | 12/1996 | |
| WO | WO 97/05903 | 2/1997 | |
| WO | WO 9705903 A2 * | 2/1997 | |
| WO | WO 97/12995 | 4/1997 | |
| WO | WO 97/13528 | 4/1997 | |
| WO | WO 9713528 A1 * | 4/1997 | |
| WO | WO 97/30731 | 8/1997 | |
| WO | WO 98/13066 A1 * | 8/1997 | |
| WO | WO 97/38728 | 10/1997 | |
| WO | WO 9738728 | 10/1997 | |
| WO | WO 98/00110 | 1/1998 | |
| WO | WO 98/00169 | 1/1998 | |
| WO | WO 9800169 A1 | 1/1998 | |
| WO | WO 98/33932 | 8/1998 | |
| WO | WO 98/49348 | 11/1998 | |
| WO | WO 99/01579 | 1/1999 | |

OTHER PUBLICATIONS

Ausubel et al. (Eds.), Short Protocols in Molecular Biology, 2nd Ed., John Wiley & Sons, New York, NY, Chapter 3, 3-100 to 3-38 (1992).

Bailly et al., "PCR-based development of DNA substrates containing modified bases: An efficient system for investigating the role of the exocyclic groups in chemical and structural recognition by minor groove binding drugs and proteins" PNAS (1996) 93:13623-13628.

Baker et al., "Cleavage of the 5' Cap Structure of mRNA by Europium(III) Macrocyclic Complex with Pendant Alcohol Groups" Journal of the American Chemical Society (1997) 119(38): 8749-8755.

Beck, "Nonradioactive Detection of DNA Using Dioxetane Chemiluminescence" Methods in Enzymology (1992) 216:143-153.

Benet et al., "Pharmacokinetics: The Dynamics of Drug Absorption, Distribution, and Elimination" Goodman & Gilman's The Pharmacological Basis of Therapetuics, 9th Ed., Hardman et al. (eds.), McGraw-Hill, New York, NY, 1996, Chapter 1, 3-9.

Berge et al., "Pharmaceutical Salts" J. Pharm. Sci. (1977) 66:1-19.

Block, "Medicated Applications" Remington's Pharmaceutical Sciences, 18th Ed., Gennaro (ed.), Mack Publishing Co., Easton, PA, 1990, Ch. 87, 1596-1614.

Block, "Pharmaceutical Dosage Forms: Disperse Systems" vol. 2, Lieberman, Rieger and Banker, Eds., Marcel Dekker, Inc., New York, NY, 1989, Chapter 9., pp. 335-378.

Branch et al., "A Good Antisense Molecule is Hard to Find" TIBS (1998) 23:45-50.

Brunton, "Agents Affecting Gastrointestinal Water Flux and Motility: Emesis and Antiemetics; Bile Acids and Pancreatic Enzymes" Goodman & Gilman's The Pharmacological Basis of Therapeutics, 9th Ed., Hardman et al. (Eds.), McGraw-Hill, New York, 1996, Chapter 38, 934-935.

Buur et al., "Penetration of 5-Fluorouracil and prodrugs across the intestine of the albino rabbit: Evidence for shift in absorption site from the upper to the lower region of the gastrointestinal tract by prodrugs" J. Controlled Release (1990) 14:43-51.

Buzayan et al., "Satellite tobacco ringspot virus RNA: A subset of the RNA sequence is sufficient for autolytic processing" PNAS (1986) 83:8859-8862.

Chollet et al., "DNA containing the base analogue 2-aminoadenine: preparation, use as hybridization probes and cleavage by restriction endonucleases" Nucl. Acids Res. (1988) 16:305-317.

Cole-Strauss et al., "Correction of the Mutation Responsible for Sickle Cell Anemia by RNA-DNA Oligonucleotide" Science (1996) 273:1386-1389.

Constantinides et al., "Formulation and Intestinal Absorption Enhancement Evaluation of Water-in-Oil Microemulsions Incorporating Medium-Chain Glycerides" Pharm. Res. (1994) 11:1385-1390.

Crooke, "Progress in Antisense Therapeutics" Hematologic Path. (1995) 9:59-72.

Crooke et al., "Progress in the development and patenting of antisense drug discovery technology" Exp. Opin. Ther. Patents (1996) 6:855-870.

Crooke et al., "Pharmacokinetic Properties of Several Novel Oligonucleotide Analogs in Mice" J. Pharmacol. Exp. Therapeutics (1996) 277:923-937.

Crooke, "Antisense '97: A roundtable on the state of the industry" Nature Biotechnology (1997) 15:522.

Crooke, "Basic Principles of Antisense Therapeutics" Antisense Research and Applications, Chapter 1, Springer-Verlag Press, Berlin, Heidelberg, New York, p. 3, Jun. 1998.

Dean et al., "Inhibition of protein kinase C-alpha expression in mice after systemic administration of phosphorothioate antisense oligodeoxynucleotides" PNAS (1994) 91:11762-11766.

DiSanto, "Bioavailability and Bioequivalency Testing" Remington's Pharmaceutical Sciences, 18th Ed., Gennaro (ed.), Mack Publishing Co., Easton, PA (1990) Ch. 76, 1451-1458.

Dustin et al., "Lymphocyte Function-Associated Antigen-1 (LFA-1) Interaction with Intercellular Adhesion Molecule-1 (ICAM-1) is One of At Least Three Mechanisms for Lymphocyte Adhesion to Cultured Endothelial Cells" J. Cell. Biol. (1988) 107:321-331.

El-Hariri et al., "The Mitigating Effect of Phosphatidylcholines on Bile Sale-and Lysophosphatidlylcholine-induced Membrane Damage" J. Pharm. Pharmacol. (1992) 44:651-654.

Ellington et al., "In vitro selection of RNA molecules that bind to specific ligands" Nature (1990) 346:818-822.

Englisch et al., "Chemically Modified Oligonucleotides as Probes and Inhibitors" Angew. Chem. Int. Ed. Eng. (1991) 30:613-629.

Forster et al., "External Guide Sequences for an RNA Enzyme" Science (1990) 249:783-786.

Forster et al., "Self-Cleavage of Virusoid RNA is Performed by the Proposed 55-Nucleotide Active Site" Cell (1987) 50:9-16.
Genetic Engineering News (1997) pp. 1 and 34.
Graham et al., "Tritium labeling of antisense oligonucleotides by exchange with tritiated water" Nucl. Acids Res. (1993) 21:3737-3743.
Guerrier-Takada et al., "Phenotypic conversion of drug-resistant bacteria to drug sensitivity" Proc. Natl. Acad. Sci. USA (1997) 94:8468-8472.
Gura, "Antisense has Growing Pains" Science (1995) 270:575-577.
Harvey, "Drug Abosrption, Action, and Disposition" Remington's Pharmaceutical Sciences, 18th Ed., Gennaro (ed.), Mack Publishing Co., Easton, PA (1990) Ch. 35, 711-715.
Haseloff et al., "Simple RNA enzymes with new and highly specific endoribonuclease activities" Nature (1988) 334(18):585-591.
Higuchi et al., "Particle Phenomena and Coarse Dispersions" Remington's Pharmaceutical Sciences, Mack Publishing Co., Easton, PA (1985) Chapter 21, pp. 301-329.
Hirahata et al., Gen To Kagaku Ryoho (1992) 19 (10 Suppl.) 1591-1594.
Ho et al., "Preparation of Microemulsions Using Polyglycerol Fatty Acid Esters as Surfactant for the Delivery of Protein Drugs" J. Pharm. Sci. (1996) 85:138-143.
Hyrup et al., "Peptide Nucleic Acids (PNA): Synthesis, Properties, and Potential Applications" Biorg. & Med. Chem. (1996) 4:5-23.
Idson, "Pharmaceutical Emulsions" in Pharmaceutical Dosage Forms: Disperse Systems, vol. 1, Lieberman, Rierger and Banker, Eds., Marcel Dekker, Inc., New York, NY (1988) Chapter 6, pp. 199-243.
Inoue et al., "Trial of Electrolyzed Strong Acid Aqueous Solution Lavage in the Treatment of Peritonitis and Intraperitoneal Abscess" Artificial Organs (1997) 21:28-31.
Jarrett, "Affinity chromatography with nucleic acid polymers" J. Chromatog. (1993) 618:315-339.
Kabanov, "A new class of antivirals: antisense oligonucleotides combined with hydrophobic substituent effectively inhibit influenza virus reproduction and synthesis of virus-specific proteins in MDCK cells" FEBS Letts. (1990) 259:327-330.
Katocs et al., "Biological Testing" Remington's Pharmaceutical Sciences, 18th Ed., Gennaro (ed.), Mack Publishing Co., Easton, PA (1990) Chapter 27: 484-494.
Komiya et al., "Quantitative Mechanistic Studies in Simultaneous Fluid Flow and Intestinal Absorption Using Steroids as Model Solutes" Int. J. Pharmaceut. (1980) 4:249-262.
Kornberg, DNA Replication (1980) W.H. Freeman & CO., San Francisco, 4-7.
Kroschwitz, "Polynucleotides" Concise Encyclopedia of Polymer Science and Engineering (1990) John Wiley & Sons, New York, 858-859.
Lee et al., "Mucosal Penetration Enhancers for Facilitation of Peptide and Protein Drug Absorption" Crit. Rev. Ther. Drug Carrier Systems (1991) 8:91-192.
Letsinger et al., "Cholesteryl-conjugated oligonucleotides: Synthesis, properties and activity as inhibitors of replication of human immunodeficiency virus in cel culture" Proc. Natl. Acad. Sci. (1989) 86:6553-6556.
Leung and Shah, "Microemulsions: An Evolving Technology for Pharmaceutical Applications" in Controlled Release of Drugs: Polymers and Aggregate Systems, Rosoff, Ed. (1989) Chapter 6, VCH Publishers, New York, pp. 185-215.
Lieb et al., "Follicular permeation of oligonucleotides" Proc. Controlled Release Soc. (1995) 22:654-655.
Manoharan et al., "Chemical Modification to Improve Uptake and Bioavailability of Antisense Oligonucleotides" Annals NY Acad. Sciences (1992) 660:306-309.
Manoharan et al., "Introduction of a Lipophilic Tether in the Minor Groove of Nucleic Acids for Antisense Applications" Bioorg. Med. Chem. Letts. (1993) 3:2765-2770.
Manoharan et al., "Lipidic Nucleic Acids" Tetrahedron Letts. (1995) 36:3651-3654.
Manoharan et al., "Oligonucleotide Conjugates: Alteration of the Pharmacokinetic Properties of Antisense Agents" Nucleosides and Nucleotides (1995) 14:969-973.

Martin, "Ein Neuer Zugang zu 2'-O-Alkylribonucleosiden and Eigenschaften deren Oligonucleotide" Helvetica Chemica Acta (1995) 78:486-504.
Miller et al., "In vitro transdermal flux and tissue distribution of interleukin 1 beta antisense methyl phosphonate oligonucleotide from topical formulations" Pharm. Res. (1993) 10:(Supp 1) S252.
Mishra et al., "Improved leishmanicidal effect of phosphorothioate antisense oligonucleotides by LDL-medicated delivery" Biochim. Et. Biophysica (1995) 1264:229-237.
Miyao et al., "Stability and Pharmacokinetic Characteristics of Oligonucleotides Modified at Terminal Linkages in Mice" Antisense Res. & Dev. (1995) 5:115-121.
Muranishi, "Absorption Enhancers" Crit. Rev. Ther. Drug Carrier Systems (1990) 7:1-33.
Nairn, Chapter 83; Blick, Chapter 87; Rudnic et al, Chapter 89; Porter, Chapter 90; and Longer et al., Chapter 91 in Remington's Pharmaceutical Sciences 18th Ed., Gennaro ed., Mack Publishing Co., Easton, PA 1990.
Nielsen et al., "Sequence-Selective Recognition of DNA by Strand Displacement with a Thymine-Substituted Polyamide" Science (1991) 254:1497-1500.
Nies et al., "Principles of Therapetuics" Goodman & Gilman's The Pharmacological Basis of Therapeutics, 9th Ed., Hardman et al., (eds.) McGraw-Hill, New York, NY (1996) Chapter 3, 43-62.
Nishihata and Rytting, "Absorption-promoting adjuvants: enhancing action on rectal absorption" Advanced Drug Delivery Reviews (1997) 28:205-228.
Nolen et al., "Percutaneous penetration of methyl phosphonate antisense oligonucleotides" International Journal of Pharmaceutics (1994) 107:169-177.
Oberhauser et al., "Effective incorporation of 2'-O-methyl-oligonucleotides into liposomes and enhanced cell association through modification with thiocholesterol" Nucl. Acids Res. (1992) 20:533-538.
Pennington et al., "Review article: artificial nutritional support for improved patient care" Aliment Pharmacol. Ther. (1995) 9:471-481.
Prosnyak et al., "Substitution of 2-Aminoadenine and 5-Mehylcytocsine for Adenine and Cytosine in Hybridization Probes Increases the Sensitivity of DNA Fingerprinting" Genomics (1994) 21:490-494.
Registry No. 144245-52-3, Apr. 1997.
Rieger. "Surfactants" in Pharmaceutical Dosage Forms: Disperse Systems, vol. 1, Lieberman, Rieger and Banker, Eds., Marcel Dekker, Inc., New York, NY (1988) Chapter 8, 285-366.
Ritschel, "Microemulsions for Improved Peptide Absorption from the Gastrointestinal Tract" Meth. Find. Exp. Clin. Pharmacol. (1991) 13:205-220.
Robertson, "Crohn's trial shows the pros of antisense" Nature Biotech. (1997) 15:209.
Rosoff, "Specialized Pharmaceutical Emulsions" in Pharmaceutical Dosage Forms: Disperse Systems, vol. 1, Lieerman, Rieger and Banker, Eds., Marcel Dekker, Inc., New York, NY (1988) Chapter 7, 245-283.
Ruth, "Oligonucleotide-Enzyme Conjugates" Methods of Molecular Biology, Agrawal (ed.) Humana Press, Totowa, NJ (1994) Chapter 6, 167-185.
Saison-Behmoaras et al., "Short modified antisense oligonucleotides directed against Ha-ras point mutation induce selective cleavage of the mRNA and inhibit T24 cells proliferation" EMBO J. (1991) 10:1111-1118.
Sambrook et al., "Preparation of Radiolabeled DNA and RNA Probes" Molecular Cloning: A Laboratory Manual (1989) 2nd. Ed., Chapter 10, 10.1 to 1.70.
Sanghvi, Chapter 15, Antisense Research and Applications, pp. 273-288, Crooke, and Lebleu, eds. CRC Press, 1993.
Schott, "Colloidal Dispersions" in Remington's Pharmaceutical Science, Mack Publishing Co., Easton, PA (1985) Chapter 20, 271-300.
Shea et al., "Synthesis, hybridization properties and antiviral activity of lipid-oligodeoxynucleotide conjugates" Nucl. Acids Res. (1990) 18:3777-3783.
Smith, "Automated Synthesis and Sequence Analysis of Biological Macromolecules" Analyt. Chem. (1988) 60:381-390.

Somogyi et al., "Evaluation of the Intestinal Absorption of Erythromycin in Man: Absolute Bioavailability Comparison with Enteric Coated Erythromycin" Pharm. Res. (1995) 12:149-154.
Svinarchuk et al., "Inhibition of HIV proliferation in MT-4 cells by antisense oligonucleotide conjugated to lipophilic groups" Biochimie (1993) 75:49-54.
Swinyard, "Gastrointestinal Drugs" Remington's Pharmaceutical Sciences, 18th Ed., Gennaro (ed.) Mack Publishing Co., Easton, PA, 1990, Chapter 39, 782-783.
Takahasi et al., "The Use of Perfluorochemical Emulsions as a Bascular Perfusate in Drug Absorption" J. Pharm. Pharmacol. (1988) 40:252-257.
Takakura et al., "Uptake Characteristics of Oligonucleotides in the Isolated Rat Liver Perfusion System" Antisense & Nuc. Acid Drug Dev. (1996) 6:177-183.
Uhlmann et al., "Antisense Oligonucleotides: A New Therapeutic Principle" Chemical Reviews (1990) 90:545-584.
U.S. Congress, Office of Technology Assessment, "The State-of-the-Art in Genetic Screening" Genetic Monitoring and Screening in the Workplace, OTO-BA-455, U.S. Government Printing Office, Washington, D.C. (1990) Chapter 5: 75-79.
Van Berge-Henegouwen, "Pharmacology of Chenodeoxycholic Acid" Gastroenterology (1977) 73:300-309.
Wahlestedt et al., "Antisense oligodeoxynucleotides to NMDA-R1 receptor channel protect cortical neurons from excitotoxicity and reduce focal ischaemic infarctions" Nature (1993) 363:260-263.
Wahlestedt et al., "Modulation of Anxiety and Heuropeptide Y-Y1 Receptors by Antisense Oligodeoxynucleotides" Science (1993) 259:528-531.
Warren et al., "Analysis and Purification of Synthetic Oligonucleotides by High-Performance Liquid Chromatography" Meth. Mol. Biol. (1994) Chapter 9, 26, 233-264.
Yamamoto et al., "A Mechanistic Study on Enhancement of Rectal Permeability to Insulin in the Albino Rabbit" J. Pharm. Exp. Ther. (1992) 263:25-31.
Yamashita et al., "Effect of Adjuvants on charge-Selective Permeability and Electrical Resistance of Rat Jejunal Membrane" J. Pharm. Sci. (1990) 79:579-583.
Yamashita et al., "Effects of diclofenac sodium and disodium ethylenediaminetetraacetate on electrical parameters of the mucosal membrane and their relation to the permeability enhancing effects in the rat jejunum" J. Pharm. Pharmacol. (1987) 39:621-626.
Zuker, "On Finding All Suboptimal Foldings of an RNA Molecule" Science (1989) 244:48-52.
Agrawal et al., "Antisense therapeutics: Is it as simple as complementary base recognition?" Molecular Medicine Today (2000) 6:72-81.
Anonymous, "ISIS Pharmaceuticals Demonstrates Efficacy in Chrohn's Disease with its Antisense Drug" Genetic Engineer. News. (1997) 17:2 pages.
Chiang et al., "Antisense Oligonucleotides Inhibit Intercellular Adhesion Molecule 1 Expression by Two Distinct Mechanisms" The Journal of Biological Chemistry (1991) 266(27): 18162-18171.
Cucco et al., "In Vitro and in Vivo Reversal of Multidrug Resistance in a Human Leukemia-resistant Cell Line by mdr1 Antisense Oligodeoxynucleotides" Cancer Research (1996) 56:4332-4337.
Del Bufalo et al., "Effect of cisplatin and c-myb antisense phosphorothioate oligodeoxynucleotides combination on a human colon carcinoma cell line in vitro and in vivo" British Journal of Cancer (1996) 74: 387-393.
DeVries et al., "Decarboxylation of L-Dopa in the Rat Isolated Vascularly perfused Small Intestine: Contribution to Systemic Elimination and Dose-dependent First Pass Effect" J. Pharm. Pharmacol. (1992) 44:311-314.
Gaffney et al., "The Influence of the Purine 2-Amino Group on DNA Conformation and Stability-II" Tetrahedron (1984) 40:3-13.
Gebeyehu et al., "Novel biotinylated nucleotide—analogs for labelling and colorimetric detection of DNA" Nucl. Acids Res. (1987) 15:4513-4534.
Gewirtz et al., "Facilitating oligonucleotide delivery: Helping antisense deliver in its promise" PNAS(USA) 93:3161-3163.
Ho et al., "Theoretical Model Studies of Drug Absorption and Transport in the GI Tract III" J. Pharm. Sci. (1972) 61:192-197.
Iversen et al., "In vivo studies with phosphorothioate oligonucleotides: pharmacokinetics prologue" Anti-Cancer Drug Des. (1991) 6:531-538.
Kararli et al., "Oral Delivery of a Renin Inhibitor Compound Using Emulsion Formulations" Pharmaceutical Res. (1992) 9:888-893.
Leonetti et al., "Antitumor Effect of c-myc Antisense Phosphorothioate Oligodeoxynucleotides on Human Melanoma Cells in Vitro and in Mice" Journal of the National Cancer Institute (1996) 88(7): 419-429.
Longer et al., "Sustained-Release Drug Deliver Systems" Remington's Pharmaceutical Sciences, 18th Ed., Gennaro (ed.), Mack Publishing Co., Easton, PA (1990) 91:1676-1693.
Manoharan et al., "Cholic Acid-Oligonucleotide Conjugates for Antisense Applications" Bioorganic Med. Chem. Letts. (1994) 4:1053-1060.
Monia et al., "Antitumor activity of a phosphorothioate antisense oligodeoxynucleotide targeted against C-raf kinase" Nature Medicine (1996) 2(6):663-675.
Monia et al., "Sequence-specific antitumor activity of a phosphorothioate oligodeoxyribonucleotide targeted to human C-raf kinase supports an antisense mechanism of action in vivo" Proc. Natl. Acad. Sci. USA (1996) 93:15481-15484.
Neurath et al., "Local administration of antisense phosphorothioate oligonucleotides to the p65 subunit of NF-kB abrogates established experimental colitis in mice" Nat. Med. (1996) 2(9):998-1004.
Oberbauer et al., "In vivo suppression of the renal Na+/Pl cotransporter by antisense oligonucleotides" Proc. Natl. Acad. Sci. (1996) 93:4903-4906.
Offensperger et al., "Antisense Therapy of Hepatitis B Virus Infection" Methods in Molecular Medicine: Antisense Therapeutics, Ed: Agrawal, Humana Press Inc., Totowa, NJ, p. 143-158.
Orkin et al., "Report and recommendations of the panel to assess the NIH investment in research on gene therapy" 1995, pp. 1-20.
Plenat et al., "Animal models of antisense oligonucleotides: lesson for use in humans" Mol. Med. Today (1996) 250-257.
Porter, "Coating of Pharmaceutical Dosage Forms" Remington's Pharmaceutical Sciences, 18th Ed., Gennaro (ed.), Mack Publishing Co., Easton PA (1990) 90:1666-1675.
Powell et al., "Intestinal perfusion of dietary levels of aluminium: association with mucosa" Gut (1994) 35:1053-1057.
Rojanasakul, "Antisense oligonucleotide therapetuics: Drug delivery and targeting" Advanced Drug Delivery Reviews (1996) 18:115-131.
Rudnic et al., "Oral Solid Dosage Forms" Remington's Pharmaceutical Sciences, 18th Ed., Gennaro (ed.), Mack Publishing Co., Easton PA (1990) Chapter 89, 1633-1665.
Stull et al., "Antigene, ribozyme and aptamer nucleic acid drugs: progress and prospects" Pharmaceut. Res. (1995) 12(4):465-483.
Sun et al., "Effects of phosphorothioated neuropeptide YY1-receptor antisense oligodeoxynucleotide in conscious rats and in human vessels" British Journal of Pharmacology (1996) 131-137.
Walker et al., "Cationic facial amphiphiles: A promising class of transfection agents" Proc. Natl. Acad. Sci. USA (1996) 93:1585-1590.
Yamashita et al., "Kinetic Analysis of the Drug Permeation Process Across the Intestinal Epithelium" Pharm. Res. (1994) 11:1646-1651.
Anderson, "Human Gene Therapy" Nature (1998) 392:25-30.
Freier et al., "The ups and downs of nucleic acid duplex stability: structure-stability studies on chemically-modified DNA:RNA duplexes" Nucl. Acids Res. (1997) 25:4429-4443.
Curone et al., "European Society of Gastrointestinal and Abdominal Radiology (ESGAR) 8th Annual Meeting and Postgraduate Course; Clinical Gastrointestinal and Abdominal Radiology: Update for the 2000's" Eur. Radiol. (1997) 7:771-809.
Hanecak et al., "Antisense Oliognucleotide Inhibition of Hepatitis C Virus Gene Expression in Transformed Hepatocytes" J. Virol. (1996) 70(8):5203-5212.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
New England Biolabs 1998/99 Catalog (cover page and pp. 121 and 284).

Reynolds et al., "Rational siRNA design for RNA interference" Nature Biotechnology (2004) 22(3):326-330.

European Supplementary Partial Search Report for Application EP 99924462.7 dated Mar. 6, 2003.

European Supplementary Search Report for Application EP 99924462.7 dated May 23, 2003.

European Supplementary Search Report for Application EP 9893407 dated May 10, 2002.

International Search Report for Application No. PCT/US1998/013574 dated Oct. 16, 1998.

International Search Report for Application No. PCT/US99/11394 dated Sep. 13, 1999.

Amidon, et al., "A Theoretical Basis for a Biopharmaceutic Drug Classification: The Correlation of in Vitro Drug Product Dissolution and in Vivo Bioavailability", Pharmaceutical Research, vol. 12, No. 3, pp. 413-420, 1995.

Uhlmann et al., "Antisense Oligonucleotides: A New Therapeutic Principle", Chemical Reviews, 1990, 90 pp. 545-584.

* cited by examiner

COMPOSITIONS AND METHODS FOR NON-PARENTERAL DELIVERY OF OLIGONUCLEOTIDES

CROSS REFERENCE TO RELATED APPLICATIONS

This application is a continuation of U.S. patent application Ser. No. 09/315,298 filed May 20, 1999, now abandoned, which is a continuation-in-part of U.S. patent application Ser. No. 09/108,673 filed Jul. 1, 1998, now U.S. Pat. No. 6,887,906, which application is a continuation-in-part of U.S. Ser. No. 08/886,829, filed Jul. 1, 1997, now abandoned.

SEQUENCE LISTING

A paper copy and a computer-readable copy of the sequence listing are provided as required under 37 C.F.R. 1.821 and are herein incorporated by reference.

FIELD OF THE INVENTION

The present invention relates to compositions and methods which enhance the local and systemic uptake and delivery of nucleic acids via non-parenteral routes of administration. More particularly, the methods and compositions enhance the transport of oligonucleotides and other nucleic acids across mucosal membranes through the use of one or more penetration enhancers. The compositions of the present invention are solutions, emulsions, and related mixtures that facilitate the uptake and delivery of oligonucleotides and other nucleic acids. The present invention is directed to the use of various fatty acids, bile salts, chelating agents and other penetration enhancers, as well as carrier compounds, to enhance the stability of oligonucleotides and other nucleic acids and/or their transport across cell walls and/or into cells. More specific objectives and advantages of the invention will hereinafter be made clear or become apparent to those skilled in the art during the course of explanation of preferred embodiments of the invention.

BACKGROUND OF THE INVENTION

Advances in the field of biotechnology have led to significant advances in the treatment of diseases such as cancer, genetic diseases, arthritis and AIDS that were previously difficult to treat. Many such advances involve the administration of oligonucleotides and other nucleic acids to a subject, particularly a human subject. The administration of such molecules via parenteral routes has been shown to be effective for the treatment of diseases and/or disorders. See, e.g., Draper et al., U.S. Pat. No. 5,595,978, Jan. 21, 1997, which discloses intravitreal injection as a means for the direct delivery of antisense oligonucleotides to the vitreous humor of the mammalian eye. See also, Robertson, *Nature Biotechnology*, 1997, 15, 209, and *Genetic Engineering News*, 1997, 15, 1, each of which discuss the treatment of Crohn's disease via intravenous infusions of antisense oligonucleotides. Non-parenteral routes for administration of oligonucleotides and other nucleic acids (such as oral or rectal delivery or other mucosal routes) offers the promise of simpler, easier and less injurious administration of such nucleic acids without the need for sterile procedures and their concomitant expenses, e.g., hospitalization and/or physician fees. There thus is a need to provide compositions and methods to enhance the availability of novel drugs such as oligonucleotides when administered via non-parenteral routes. It is desirable that such new compositions and methods provide for the simple, convenient, practical and optimal non-parenteral delivery of oligonucleotides and other nucleic acids.

SUMMARY OF THE INVENTION

In accordance with the present invention, compositions and methods are provided for the non-parenteral delivery and mucosal penetration of nucleic acids in an animal. In particular, the present invention provides compositions and methods for modulating the production of selected proteins or other biological phenomena in an animal, which involves the administration of an oligonucleotide, especially an antisense oligonucleotide, via non-parenteral means to an animal, thereby circumventing the complications and expense which may be associated with intravenous and other parenteral modes of in vivo administration. "Non-parenteral administration" refers to the contacting, directly or otherwise, to all or a portion of the alimentary canal, skin, eyes, pulmonary tract, urethra or vagina of an animal. Compositions of the present invention may be a mixture of components or phases as are present in emulsions (including microemulsions and creams), and related formulations comprising two or more phases.

In one aspect, the present invention provides pharmaceutical compositions comprising at least one nucleosidic moiety such as a nucleoside, nucleotide, or nucleic acid in a solution or emulsion. The nucleic acid can be a ribozyme, a PNA, or an aptamer, but preferably is an oligonucleotide such as, for example, an oligonucleotide that modulates expression of a cellular adhesion protein, modulates a rate of cellular proliferation, or has biological activity against eukaryotic pathogens or retroviruses.

In certain embodiments, solutions according to the invention consist essentially of the nucleosidic moiety and a solvent comprising, for example, saline solution or cocoa butter. Emulsions according to the invention include oil-in-water emulsions, water-in-oil emulsions, oil-in-water-in-oil emulsions, and water-in-oil-in-water emulsions.

In certain embodiments, the pharmaceutical compositions of the invention further comprise a penetration enhancer such as a fatty acid, a bile salt, a chelating agent, a surfactant, and a non-surfactant such as an unsaturated cyclic urea, a 1-alkylalkanone, a 1-alkenylazacyclo-alakanone, or a steroidal anti-inflammatory agent.

Also provided are methods for treating an animal comprising administering to the animal a therapeutically effective amount of a pharmaceutical composition according to the invention. The composition can be administered by, for example, buccal, sublingual, endoscopic, rectal, oral, vaginal, topical, pulmonary, or urethral routes. In preferred embodiments, the compositions of the invention are administered rectally means of an enema or a suppository.

Because of the advantages of non-parenteral delivery of drugs of the antisense class, the compositions and methods of the invention can be used in therapeutic methods as explained in more detail herein. The compositions and methods herein provided may also be used to examine the function of various proteins and genes in an animal, including those essential to animal development. The methods of the invention can be used, for example, for the treatments of animals that are known or suspected to suffer from diseases such as ulcerative colitis, Chrohn's disease, inflammatory bowel disease, or undue cellular proliferation.

DETAILED DESCRIPTION OF THE INVENTION

The invention provides compositions and methods for the local as well as systemic delivery of oligonucleotides and other nucleic acids to an animal via non-parenteral means. In particular, the present invention provides compositions and methods for modulating the in vivo expression of a gene in an animal through the non-parenteral administration of an antisense oligonucleotide, thereby circumventing the complications and expense which may be associated with intravenous and other parenteral routes of administration.

Enhanced bioavailability of oligonucleotides and other nucleic acids is achieved via the non-parenteral administration of the compositions and methods of the present invention. The term "bioavailability" refers to a measurement of what portion of an administered drug reaches the circulatory system when a non-parenteral mode of administration is used to introduce the drug into an animal. The term is used for drugs whose efficacy is related to the blood concentration achieved, even if the drug's ultimate site of action is intracellular (van Berge-Henegouwen et al., *Gastroenterol.*, 1977, 73, 300). Traditionally, bioavailability studies determine the degree of intestinal absorption of a drug by measuring the change in peripheral blood levels of the drug after an oral dose (DiSanto, Chapter 76 In. *Remington's Pharmaceutical Sciences*, 18th Ed., Gennaro, ed., Mack Publishing Co., Easton, Pa., 1990, pages 1451-1458). The area under the curve ($AUC_0$) is divided by the area under the curve after an intravenous (i.v.) dose ($AUC_{iv}$) and the quotient is used to calculate the fraction of drug absorbed. This approach cannot be used, however, with compounds which have a large "first pass clearance," i.e., compounds for which hepatic uptake is so rapid that only a fraction of the absorbed material enters the peripheral blood. For such compounds, other methods must be used to determine the absolute bioavailability (van Berge-Henegouwen et al., *Gastroenterol.*, 1977, 73, 300). With regards to oligonucleotides, studies suggest that they are rapidly eliminated from plasma and accumulate mainly in the liver and kidney after i.v. administration (Miyao et al., *Antisense Res. Dev.*, 1995, 5, 115; Takakura et al., *Antisense & Nucl. Acid Drug Dev.*, 1996, 6, 177).

Another "first pass effect" that applies to orally administered drugs is degradation due to the action of gastric acid and various digestive enzymes. Furthermore, the entry of many high molecular weight active agents (such as peptides, proteins and oligonucleotides) and some conventional and/or low molecular weight drugs (e.g., insulin, vasopressin, leucine enkephalin, etc.) through mucosal routes (such as oral, pulmonary, buccal, rectal, transdermal, vaginal and ocular) to the bloodstream is frequently obstructed by poor transport across epithelial cells and concurrent metabolism during transport. This type of degradative metabolism is known for oligonucleotides and nucleic acids. For example, phosphodiesterases are known to cleave the phosphodiester linkages of oligonucleotides and many other modified linkages present in synthetic oligonucleotides and nucleic acids.

One means of ameliorating first pass clearance effects is to increase the dose of administered drug, thereby compensating for proportion of drug lost to first pass clearance. Although this may be readily achieved with i.v. administration by, for example, simply providing more of the drug to an animal, other factors influence the bioavailability of drugs administered via non-parenteral means. For example, a drug may be enzymatically or chemically degraded in the alimentary canal or blood stream and/or may be impermeable or semipermeable to various mucosal membranes.

It has now been found that oligonucleotides can be introduced effectively into animals via non-parenteral means through coadministration of "mucosal penetration enhancers," also known as "absorption enhancers" or simply as "penetration enhancers". These are substances which facilitate the transport of a drug across mucous membrane(s) associated with the desired mode of administration.

A "pharmaceutically acceptable" component of a formulation of the invention is one which, when used together with excipients, diluents, stabilizers, preservatives and other ingredients are appropriate to the nature, composition and mode of administration of a formulation. Accordingly it is desired to select penetration enhancers which facilitate the uptake of oligonucleotides, without interfering with the activity of the oligonucleotides and in a manner such that the same can be introduced into the body of an animal without unacceptable side-effects such as toxicity, irritation or allergic response.

The present invention provides compositions comprising one or more pharmaceutically acceptable penetration enhancers, and methods of using such compositions, which result in the improved bioavailability of nucleic acids administered via non-parenteral modes of administration. Heretofore, certain penetration enhancers have been used to improve the bioavailability of certain drugs. See Muranishi, *Crit. Rev. Ther. Drug Carrier Systems*, 1990, 7, 1 and Lee et al., *Crit. Rev. Ther. Drug Carrier Systems*, 1991, 8, 91. However, it is generally viewed to be the case that effectiveness of such penetration enhancers is unpredictable. Therefore, it has been surprisingly found that the uptake and delivery of oligonucleotides, relatively complex molecules which are known to be difficult to administer to animals and man, can be greatly improved even when administered by non-parenteral means through the use of a number of different classes of penetration enhancers.

The effective non-parenteral use and administration of compositions of the present invention involves consideration of a number of different aspects about drug therapy. One important consideration when using the compositions and methods of the present invention is the mode of administration of the pharmaceutical composition containing the therapeutic oligonucleotide or other nucleic acid. Administration typically is either parenteral or non-parenteral. Non-parenteral modes of administration include, but are not limited to, buccal, sublingual, endoscopic, oral, rectal, transdermal, topical, nasal, intratracheal, pulmonary, urethral, vaginal, and ocular. When administered by such non-parenteral modes the methods and composition of the present invention can deliver drug both locally and systemically as desired.

A second consideration of importance when using the compositions and methods of the present invention is the use and nature of penetration enhancers and carriers. Penetration enhancers facilitate the transport of drug molecules, for example, oligonucleotides and other nucleic acids, across mucosal and other epithelial cell membranes. Penetration enhancers include, but are not limited to, members of molecular classes such as surfactants, fatty acids, bile salts, chelating agents, and non-chelating non-surfactant molecules. Carriers are inert molecules that may be included in the compositions of the present invention to interfere with processes that lead to reduction in the levels of bioavailable nucleic acid or oligonucleotide drug.

A third consideration of importance to the compositions and methods of the present invention is the nature of oligonucleotide or other nucleic acid used. Oligonucleotides of the present invention may be, but are not limited to, those nucleic acids bearing modified linkages, modified nucleobases, or modified sugars, and chimeric nucleic acids.

A fourth consideration of importance in the present invention is the nature of the composition. Pharmaceutical compositions of the present invention include, but are not limited to, solutions, emulsions (including microemulsions and creams), and liposome-containing formulations. These compositions may be generated from a variety of components that include, but are not limited to, preformed liquids, self-emulsifying solids and self-emulsifying semisolids. The compositions of the present invention may be formulated into any of many possible dosage forms such as, but not limited to, tablets, capsules, liquid syrups, soft gels, suppositories, and enemas.

A fifth consideration of importance to the compositions and methods of the present invention is the means by which such compositions may be administered. Thus the dose, method of administration or application, and the use of additives are all worthy of consideration in this regard. Further, the methods and compositions of the present invention may be used to ameliorate a variety of diseases via local or systemic treatment. Such local or systemic treatment may be accomplished using the methods and compositions of the present invention via modes of administration that include, but are not limited to, buccal, sublingual, endoscopic, oral, rectal, transdermal, topical, nasal, pulmonary, urethral, vaginal, and ocular modes.

A sixth consideration of importance to the compositions and methods of the present invention is their applicability to bioequivalents of oligonucleotides and other nucleic acids such as, but not limited to, oligonucleotide prodrugs, deletion derivatives, conjugates, aptamers, and ribozymes.

The present invention provides compositions and methods for local and systemic delivery of one or more nucleic acids to an animal via non-parenteral administration. For purposes of the invention, the term "animal" is meant to encompass humans as well as other mammals, as well as reptiles, fish, amphibians, and birds. The term "non-parenteral delivery" refers to the administration, directly or otherwise, of the drug via a non-invasive procedure which typically does not entail the use of a syringe and needle. Non-parenteral administration may be, but is not limited to, delivery of the drug via the alimentary canal or via transdermal, topical, nasal, pulmonary, urethral, vaginal or ocular routes. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastro-intestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the nucleic acid(s) so administered.

In addition, iontophoresis (transfer of ionic solutes through biological membranes under the influence of an electric field) (Lee et al., *Critical Reviews in Therapeutic Drug Carrier Systems*, 1991, p. 163), phonophoresis or sonophoresis (use of ultrasound to enhance the absorption of various therapeutic agents across biological membranes, notably the skin and the cornea) (Lee et al., *Critical Reviews in Therapeutic Drug Carrier Systems*, 1991, p. 166), and optimization of vehicle characteristics relative to dose deposition and retention at the site of administration (Lee et al., *Critical Reviews in Therapeutic Drug Carrier Systems*, 1991, p. 168) may be useful methods for enhancing the transport of drugs across mucosal sites in accordance with the present invention.

Delivery of a drug via the oral mucosa, as in the case of buccal and sublingual administration, has several desirable features, including, in many instances, a more rapid rise in plasma concentration of the drug than via oral delivery (Harvey, Chapter 35 In. *Remington's Pharmaceutical Sciences*, 18th Ed., Gennaro, ed., Mack Publishing Co., Easton, Pa., 1990, page 711). Furthermore, because venous drainage from the mouth is to the superior vena cava, this route also bypasses rapid first-pass metabolism by the liver. Both of these features contribute to the sublingual route being the mode of choice for drugs like nitroglycerin (Benet et al., Chapter 1 In: *Goodman & Gilman's The Pharmacological Basis of Therapeutics*, 9th Ed., Hardman et al., eds., McGraw-Hill, New York, N.Y., 1996, page 7).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho*, 1992, 19(10 Suppl.), 1591). Pharmaceutical compositions, including liposomal formulations, can be delivered directly into portions of the alimentary canal, such as, e.g., the duodenum (Somogyi et al., *Pharm. Res.*, 1995, 12, 149) or the gastric submucosa (Akamo et al., *Japanese J. Cancer Res.*, 1994, 85, 652) via endoscopic means. Gastric lavage devices (Inoue et al., *Artif. Organs*, 1997, 21, 28) and percutaneous endoscopic feeding devices (Pennington et al., *Ailment Pharmacol Ther.*, 1995, 9, 471) can also be used for direct alimentary delivery of pharmaceutical compositions.

Drugs administered by the oral route can often be alternatively administered by the lower enteral route, i.e., through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 In: *Remington's Pharmaceutical Sciences*, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 In: *Goodman & Gilman's The Pharmacological Basis of Therapeutics*, 9th Ed., Hardman et al., eds., McGraw-Hill, New York, N.Y., 1996).

The preferred method of non-parenteral administration for most drugs is oral delivery. This is typically the most convenient route for access to the systemic circulation. Absorption from the alimentary canal is governed by factors that are generally applicable, e.g., surface area for absorption, blood flow to the site of absorption, the physical state of the drug and its concentration at the site of absorption (Benet et al., Chapter 1 In: *Goodman & Gilman's The Pharmacological Basis of Therapeutics*, 9th Ed., Hardman et al., eds., McGraw-Hill, New York, N.Y., 1996, pages 5-7). A significant factor which may limit the oral bioavailability of a drug is the degree of "first pass effects." For example, some substances have such a rapid hepatic uptake that only a fraction of the material absorbed enters the peripheral blood (Van Berge-Henegouwen et al., *Gastroenterology*, 1977, 73:300). The compositions and methods of the invention circumvent, at least partially, such first pass effects by providing improved uptake of nucleic acids by, e.g., causing the hepatic uptake system to become saturated and allowing a significant portion of the nucleic acid so administered to reach the peripheral circulation.

Topical administration is often chosen when local delivery of a drug is desired at, or immediately adjacent to the point of application of the drug composition or formulation. Although occasionally enough drug is absorbed into the systemic circulation to cause systemic effects, topical routes generally are not effective for systemic therapy. Three general types of topical routes of administration are recognized, topical administration of a drug composition to mucous membranes, skin or eyes.

Drugs that are applied to the mucous membranes produce primarily local effects. This route of administration includes application of drug compositions to mucous membranes of the conjunctiva, nasopharynx, oropharynx, vagina, colon, urethra, and urinary bladder. Absorption of drugs occurs rapidly through mucous membranes and is an effective route for localized therapy and, on occasion, for systemic therapy.

Transdermal drug delivery is a valuable route for the administration of lipid soluble therapeutics. It has been recognized that the dermis is more permeable than the epidermis and therefore absorption of drugs is much more rapid through abraded, burned or denuded skin. Inflammation and other physiologic conditions that increase blood flow to the skin also enhance absorption via the transdermal route. Absorption by this route may be enhanced via the use of an oily vehicle (inunction) or through the use of penetration enhancers. Hydration of the skin and the use of controlled release topical patches are also effective ways to administer drugs via the transdermal route. This route provides a means to deliver the drug for both systemic and local therapy.

Ocular delivery of drugs is especially useful for the local treatment of eye infections or abnormalities. The drug is typically administered via instillation and absorption of the drug occurs through the cornea. Corneal infection or trauma may thus result in more rapid absorption. Ophthalmic delivery systems that provide prolonged duration of action (e.g., suspensions and ointments) and ocular inserts that provide continuous delivery of low amounts of drugs are useful additions to ophthalmic therapy. The ocular delivery of drugs results in predominantly local effects. Systemic absorption that results from drainage via the nasolachrimal canal is limited and few systemic side effects are typically observed.

The present invention employs various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., *Critical Reviews in Therapeutic Drug Carrier Systems,* 1991, p. 92). Each of these classes is discussed in more detail in the following paragraphs. Carrier substances (or simply "carriers"), which reduce first pass effects by, e.g., saturating the hepatic uptake system, are also herein described.

In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., *Critical Reviews in Therapeutic Drug Carrier Systems,* 1991, page 92); and perfluorohemical emulsions, such as FC-43 (Takahashi et al., *J. Pharm. Pharmacol.,* 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems,* 1991, page 92; Muranishi, *Critical Reviews in Therapeutic Drug Carrier Systems,* 1990, 7, 1; El-Hariri et al., *J. Pharm. Pharmacol.,* 1992, 44, 651).

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 In: *Goodman & Gilman's The Pharmacological Basis of Therapeutics,* 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782-783; Muranishi, *Critical Reviews in Therapeutic Drug Carrier Systems,* 1990, 7, 1; Yamamoto et al., *J. Pharm. Exp. Ther.,* 1992, 263, 25; Yamashita et al., *J. Pharm. Sci.,* 1990, 79, 579).

In a particular embodiment, penetration enhancers useful in the present invention are mixtures of penetration enhancing compounds. For example, a particularly preferred penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Preferred penetration enhancer mixtures comprise about 5-95% of bile acid or salt(s) UDCA and/or CDCA with 5-95% capric and/or lauric acid. Particularly preferred are mixtures of the sodium salts of UDCA, capric acid and lauric acid in a ratio of about 1:2:2 respectively. In another particularly preferred embodiment Chelating agents, as used in connection with the present invention, can be defined to be compounds that remove metallic ions from solution by forming complexes therewith, with the result that absorption of oligonucelotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.,* 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1; Buur et al., *J. Control Rel.*, 1990, 14, 43).

As used herein, non-chelating non-surfactant penetration enhancers may be defined as compounds that demonstrate insignificant activity as chelating agents or as surfactants but that nonetheless enhance absorption of oligonucelotides through the alimentary and other mucosal membranes (Muranishi, *Critical Reviews in Therapeutic Drug Carrier Systems*, 1990, 7, 1). This class of penetration enhancers includes, but is not limited to, unsaturated cyclicureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), can be used.

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115; Takakura et al., *Antisense & Nucl. Acid Drug Dev.*, 1996, 6, 177).

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

The present invention employs oligonucleotides for use in antisense modulation of the function of DNA or messenger RNA (mRNA) encoding a protein the modulation of which is desired, and ultimately to regulate the amount of such a protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, turnover or degradation of the mRNA and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as modified oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of repeating units generically known as a nucleotides. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the carbon 5 (5') position of the sugar of a first nucleotide and the carbon 3 (3') position of a second, adjacent nucleotide. A "nucleoside" is the combination of (1) a nucleobase and (2) a sugar in the absence of (3) a phosphate moiety (Kornberg, A., *DNA Replication*, W.H. Freeman & Co., San Francisco, 1980, pages 4-7). The backbone of an oligonucleotide positions a series of bases in a specific order; the written representation of this series of bases, which is conventionally written in 5' to 3' order, is known as a nucleotide sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. Antisense oligonucleotides have also been used as diagnostic aids based on their specific binding or hybridization to DNA or mRNA that are present in certain disease states and due to the high degree of sensitivity that hybridization based assays and amplified assays that utilize some of polymerase chain reaction afford. The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections. Other examples of antisense oligonucleotides are provided herein.

Further, oligonucleotides used in the compositions of the present invention may be directed to modify the effects of mRNAs or DNAs involved in the synthesis of proteins that regulate adhesion of white blood cells and to other cell types. The adherence of white blood cells to vascular endothelium appears to be mediated in part if not in toto by five cell adhesion molecules ICAM-1, ICAM-2, ELAM-1, VCAM-1 and GMP-140. Dustin and Springer, *J. Cell. Biol.* 1987, 107, 321. Such antisense oligonucleotides are designed to hybridize either directly to the mRNA or to a selected DNA portion encoding intercellular adhesion molecule-1 (ICAM-1), endothelial leukocyte adhesion molecule-1 (ELAM-1, or E-selectin), and vascular cell adhesion molecule-1 (VCAM-1) as disclosed in U.S. Pat. No. 5,514,788 (Bennett et al., May 7, 1996) and U.S. Pat. No. 5,591,623 (Bennett et al., Jan. 7, 1997), and pending U.S. patent application Ser. No. 08/440,740 (filed May 12, 1995) and Ser. No. 09/062,416 (filed Apr. 17, 1998). These oligonucleotides have been found to modulate the activity of the targeted mRNA or DNA, leading to the modulation of the synthesis and metabolism of specific cell adhesion molecules, and thereby result in palliative and therapeutic effects. Inhibition of ICAM-1, VCAM-1 and ELAM-1 expression is expected to be useful for the treatment of inflammatory diseases, diseases with an inflammatory component, allograft rejection, psoriasis and other skin diseases, inflammatory bowel disease, cancers and their metastases, and viral infection. Methods of modulating cell adhesion comprising contacting the animal with an oligonucleotide composition of the present invention are provided.

The antisense compounds used as exemplary biologically active nucleic acids in the studies detailed herein are as follows:

ISIS 2302 is a 2'-deoxyoligonucleotide having a phosphorothioate backbone and the sequence 5'-GCC-CAA-GCT-GGC-ATC-CGT-CA-3' (SEQ ID NO: 1). ISIS 2302 is targeted to the 3'-untranslated region (3'-UTR) of the human ICAM-1 gene. ISIS 2302 is described in U.S. Pat. Nos. 5,514,788 and 5,591,623, hereby incorporated by reference.

ISIS 15839 is a phosphorothioate isosequence "hemimer" derivative of ISIS 2302 having the structure 5'-GCC-CAA-GCT-GGC-ATC-CGT-CA-3' (SEQ ID NO: 1), wherein emboldened "C" residues have 5-methylcytosine (m5c) bases and wherein the emboldened, double-underlined residues further comprise a 2'-methoxyethoxy modification (other residues are 2'-deoxy). ISIS 15839 is described in co-pending U.S. patent application Ser. No. 09/062,416, filed Apr. 17, 1998, hereby incorporated by reference.

ISIS 1939 is a 2'-deoxyoligonucleotide having a phosphorothioate backbone and the sequence 5'-CCC-CCA-CCA-CTT-CCC-CTC-TC-3' (SEQ ID NO:2). ISIS 1939 is targeted to the 3'-untranslated region (3'-UTR) of the human ICAM-1 gene. ISIS 1939 is described in U.S. Pat. Nos. 5,514,788 and 5,591,623, hereby incorporated by reference.

Examination of the predicted RNA secondary structure of the human ICAM-1 mRNA 3'-untranslated region (M. Zuker, *Science* 1989, 244, 48) surprisingly suggested that both ISIS 1939 and ISIS 2302 hybridize to sequences predicted to be in a stable stem-loop structure of the mRNA. Current dogma suggests that when designing antisense oligonucleotides regions of RNA secondary structure should be avoided. Thus, ISIS 1939 and ISIS 2302 would not have been predicted to inhibit ICAM-1 expression.

ISIS 2302 (SEQ ID NO: 1) has been found to inhibit ICAM-1 expression in human umbilical vein cells, human lung carcinoma cells (A549), human epidermal carcinoma cells (A431), and human keratinocytes. ISIS 2302 has also demonstrated specificity for its target ICAM-1 over other potential nucleic acid targets such as HLA-A and HLA-B. ISIS 1939 (SEQ ID NO:2) and ISIS 2302 markedly reduced ICAM-1 expression, as detected by northern blot analysis to determine mRNA levels, in C8161 human melanoma cells. In an experimental metastasis assay, ISIS 2302 decreased the metastatic potential of C8161 cells, and eliminated the enhanced metastatic ability of C8161 cells resulting from TNF-α treatment. ISIS 2302 has also shown significant biological activity in animal models of inflammatory disease. The data from animal testing has revealed strong anti-inflammatory effects of ISIS 2302 in a number of inflammatory diseases including Crohn's disease, rheumatoid arthritis, psoriasis, ulcerative colitis, and kidney transplant rejection. When tested on humans, ISIS 2302 has shown good safety and activity against Crohn's disease. Further ISIS 2302 has demonstrated a statistically significant steroid-sparing effect on treated subjects such that even after five months post-treatment subjects have remained weaned from steroids and in disease remission. This is a surprising and significant finding of ISIS 2302's effects.

The oligonucleotides used in the compositions of the present invention preferably comprise from about 8 to about 30 nucleotides. It is more preferred that such oligonucleotides comprise from about 10 to about 25 nucleotides.

Antisense oligonucleotides employed in the compositions of the present invention may also be used to determine the nature, function and potential relationship of various genetic components of the body to normal or abnormal body states of animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences*, 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. By providing compositions and methods for the simple non-parenteral delivery of oligonucleotides and other nucleic acids, the present invention overcomes these and other shortcomings.

Specific examples of some preferred modified oligonucleotides envisioned for use in the compositions of the present invention include oligonucleotides containing modified backbones or non-natural intersugar linkages. As defined in this specification, oligonucleotides having modified backbones include those that retain a phosphorus atom in the backbone and those that have an atom (or group of atoms) other than a phosphorus atom in the backbone. For the purposes of this specification, and as sometimes referenced in the art, modified oligonucleotides that do not have a phosphorus atom in their intersugar backbone, including peptide nucleic acids (PNAs) are also be considered to be oligonucleotides.

Specific oligonucleotide chemical modifications are described in the following subsections. It is not necessary for all positions in a given compound to be uniformly modified, and in fact more than one of the following modifications may be incorporated in a single antisense compound or even in a single residue thereof, for example, at a single nucleoside within an oligonucleotide.

A. Modified Linkages: Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thiono-alkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus atom containing linkages include, but are not limited to, U.S. Pat. Nos. 3,687,808; 4,469,863; 4,476, 301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, certain of which are commonly owned with this application, and each of which is herein incorporated by reference.

Preferred modified oligonucleotide backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, certain of which are commonly owned with this application, and each of which is herein incorporated by reference.

In other preferred oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497.

Some preferred embodiments of the present invention may employ oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

B. Modified Nucleobases: The oligonucleotides employed in the compositions of the present invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2EC (Id., pages 276-278) and are presently preferred base substitutions, even more particularly when combined with 2'-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, certain of which are commonly owned, and each of which is herein incorporated by reference, and commonly owned U.S. patent application Ser. No. 08/762,488, filed on Dec. 10, 1996, also herein incorporated by reference.

C. Sugar Modifications: The oligonucleotides employed in the compositions of the present invention may additionally or alternatively comprise one or more substituted sugar moieties. Preferred oligonucleotides comprise one of the following at the 2' position: OH; F; O-, S-, or N-alkyl, O-, S-, or N-alkenyl, or O, S- or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$ and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'-O—$CH_2CH_2OCH_3$, also known as 2'-O-(2-methoxyethyl) or 2'-MOE] (Martin et al., *Helv. Chim. Acta*, 1995, 78, 486), i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'-O—$CH_3$), 2'-aminopropoxy (2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, certain of which are commonly owned, and each of which is herein incorporated by reference, and commonly owned U.S. patent application Ser. No. 08/468,037, filed on Jun. 5, 1995, also herein incorporated by reference.

D. Other Modifications: Additional modifications may also be made at other positions on the oligonucleotide, particularly the 3' position of the sugar on the 3' terminal nucleotide and the 5' position of 5' terminal nucleotide. For example, one additional modification of the oligonucleotides employed in the compositions of the present invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned, and each of which is herein incorporated by reference.

A preferred conjugate imparting improved absorption of oligonucleotides in the gut is folic acid. Accordingly, there is provided a composition for oral administration comprising an oligonucleotide and a carrier wherein said oligonucleotide is conjugated to folic acid. Folic acid (folate) may be conjugated to the 3' or 5' termini of oligonucleotides, to a nucleobase or to a 2' position of any of the sugar residues in the chain. Conjugation may be via any suitable chemical linker utilitizing functional groups on the oligonucleotide and folate. Oligonucleotide-folate conjugates and methods in preparing are described in copending U.S. patent application Ser. No. 09/098,166 (filed Jun. 16, 1998) and Ser. No. 09/275,505 (filed Mar. 24, 1999) both incorporated herein by reference.

E. Chimeric Oligonucleotides: The present invention also includes compositions employing antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate oligodeoxynucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy-substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy-substituted), or vice-versa.

A number of chemical modifications to oligonucleotides that confer greater oligonucleotide:RNA duplex stability have been described by Freier et al. (*Nucl. Acids Res.*, 1997, 25, 4429). Such modifications are preferred for the RNase H-refractory portions of chimeric oligonucleotides and may generally be used to enhance the affinity of an antisense compound for a target RNA.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned, and each of which is herein incorporated by reference, and commonly owned and allowed U.S. patent application Ser. No. 08/465,880, filed on Jun. 6, 1995, also herein incorporated by reference.

The present invention also includes compositions employing oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoamidate or phosphotriester linkages (Cook, U.S. Pat. Nos. 5,212,295 and 5,521, 302).

The present invention further encompasses compositions employing ribozymes. Synthetic RNA molecules and derivatives thereof that catalyze highly specific endoribonuclease activities are known as ribozymes. (See, generally, U.S. Pat. No. 5,543,508 to Haseloff et al., issued Aug. 6, 1996, and U.S. Pat. No. 5,545,729 to Goodchild et al., issued Aug. 13, 1996.) The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.*, 1986, 83, 8859; Forster et al., *Cell,* 1987, 50, 9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

Other biologically active oligonucleotides may be formulated in the compositions of the invention and used for therapeutic, palliative or prophylactic purposes according to the methods of the invention. Such other biologically active oligonucleotides include, but are not limited to, antisense compounds including, inter alia, antisense oligonucleotides, antisense PNAs and ribozymes (described supra) and EGSs, as well as aptamers and molecular decoys (described infra).

Sequences that recruit RNase P are known as External Guide Sequences, hence the abbreviation "EGS." EGSs are antisense compounds that direct of an endogenous nuclease (RNase P) to a targeted nucleic acid (Forster et al., *Science,* 1990, 249, 783; Guerrier-Takada et al., *Proc. Natl. Acad. Sci. USA,* 1997, 94, 8468).

Antisense compounds may alternatively or additionally comprise a synthetic moiety having nuclease activity covalently linked to an oligonucleotide having an antisense sequence instead of relying upon recruitment of an endogenous nuclease. Synthetic moieties having nuclease activity include, but are not limited to, enzymatic RNAs (as in ribozymes), lanthanide ion complexes, and the like (Haseloff et al., *Nature,* 1988, 334, 585; Baker et al., *J. Am. Chem. Soc.,* 1997, 119, 8749).

Aptamers are single-stranded oligonucleotides that bind specific ligands via a mechanism other than Watson-Crick base pairing. Aptamers are typically targeted to, e.g., a protein and are not designed to bind to a nucleic acid (Ellington et al., *Nature,* 1990, 346, 818).

Molecular decoys are short double-stranded nucleic acids (including single-stranded nucleic acids designed to "fold back" on themselves) that mimic a site on a nucleic acid to which a factor, such as a protein, binds. Such decoys are expected to competitively inhibit the factor; that is, because the factor molecules are bound to an excess of the decoy, the concentration of factor bound to the cellular site corresponding to the decoy decreases, with resulting therapeutic, palliative or prophylactic effects. Methods of identifying and constructing nucleic acid decoy molecules are described in, e.g., U.S. Pat. No. 5,716,780 to Edwards et al.

Another type of bioactive oligonucleotide is an RNA-DNA hybrid molecule that can direct gene conversion of an endogenous nucleic acid (Cole-Strauss et al., *Science,* 1996, 273, 1386).

Examples of specific oligonucleotides and the target genes to which they inhibit, which may be employed in formulations of the present invention include:

ISIS-2302  GCCCA AGCTG GCATC  (SEQ ID NO: 1) ICAM-1
           CGTCA

-continued

ISIS-15839  GCCCA AGCTG GCATC  (SEQ ID NO: 1) ICAM-1
            CGTCA

ISIS-1939   CCCCC ACCAC TTCCC  (SEQ ID NO: 2) ICAM-1
            CTCTC

ISIS-2922   GCGTT TGCTC TTCTT  (SEQ ID NO: 48)HCMV
            CTTGC G

ISIS-13312  GCGTT TGCTC TTCTT  (SEQ ID NO: 48)HCMV
            CTTGC G

ISIS-3521   GTTCT CGCTG GTGAG  (SEQ ID NO: 49)PKCα
            TTTCA

ISIS-9605   GTTCT CGCTG GTGAG  (SEQ ID NO: 49)PKCα
            TTTCA

ISIS-9606   GTTCT CGCTG GTGAG  (SEQ ID NO: 49)PKCα
            TTTCA

ISIS-14859  AACTT GTGCT TGCTC  (SEQ ID NO: 50)PKCα

ISIS-2503   TCCGT CATCG CTCCT  (SEQ ID NO: 16)Ha-ras
            CAGGG

ISIS-5132   TCCCG CCTGT GACAT  (SEQ ID NO: 19)c-raf
            GCATT

ISIS-14803  GTGCT CATGG TGCAC  (SEQ ID NO: 51)HCV
            GGTCT

ISIS-28089  GTGTG CCAGA CACCC  (SEQ ID NO: 52)TNFα
            TATCT

ISIS-104838 GCTGA TTAGA GAGAG  (SEQ ID NO: 53)TNFα
            GTCCC

ISIS-2105   TTGCT TCCAT CTTCC  (SEQ ID NO: 54)HPV
            TCGTC wherein (i) each oligo backbone linkage is a phosphorothioate linkage (except ISIS-9605) and (ii) each sugar is 2'-deoxy unless represented in bold font in which case it incorporates a 2'-O-methoxyethyl group and iii) underlined cytosine nucleosides incorporate a 5-methyl substituent on their nucleobase. ISIS-9605 incorporates natural phosphodiester bonds at the first five and last five linkages with the remainder being phosphorothioate linkages.

F. Synthesis: The oligonucleotides used in the compositions of the present invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

1. Teachings regarding the synthesis of particular modified oligonucleotides may be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

2. Bioequivalents: The compositions of the present invention encompass any pharmaceutically acceptable compound which, upon administration to an animal including a human, is capable of providing (directly or indirectly) the biologically active metabolite or residue thereof. Accordingly, for example, the disclosure is also drawn to "prodrugs" and "pharmaceutically acceptable salts" of the antisense compounds of the invention and other bioequivalents.

A. Oligonucleotide Prodrugs: The oligonucleotide and nucleic acid compounds employed in the compositions of the present invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the antisense compounds may be prepared as SATE [(S-acetyl-2-thioethyl) phosphate] derivatives according to the methods disclosed in WO 93/24510 (Gosselin et al., published Dec. 9, 1993).

B. Pharmaceutically Acceptable Salts: The term "pharmaceutically acceptable salts" refers to physiologically and pharmaceutically acceptable salts of the oligonucleotide and nucleic acid compounds employed in the compositions of the present invention (i.e., salts that retain the desired biological activity of the parent compound and do not impart undesired toxicological effects thereto).

Pharmaceutically acceptable base addition salts are formed with metals or amines, such as alkali and alkaline earth metals or organic amines. Examples of metals used as cations are sodium, potassium, magnesium, calcium, ammonium, polyamines such as spermine and spermidine, and the like. Examples of suitable amines are chloroprocaine, choline, N,N'-dibenzylethylenediamine, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

During the process of oligonucleotide synthesis, nucleoside monomers are attached to the chain one at a time in a repeated series of chemical reactions such as nucleoside monomer coupling, oxidation, capping and detritylation. The stepwise yield for each nucleoside addition is above 99%. That means that less than 1% of the sequence chain failed to be generated from the nucleoside monomer addition in each step as the total results of the incomplete coupling followed by the incomplete capping, detritylation and oxidation (Smith, *Anal. Chem.*, 1988, 60, 381A). All the shorter oligonucleotides, ranging from (n-1), (n-2), etc., to 1-mers (nucleotides), are present as impurities in the n-mer oligonucleotide product. Among the impurities, (n-2)-mer and shorter oligonucleotide impurities are present in very small amounts and can be easily removed by chromatographic purification (Warren et al., Chapter 9 In: *Methods in Molecular Biology, Vol. 26. Protocols for Oligonucleotide Conjugates*, Agrawal, S., Ed., 1994, Humana Press Inc., Totowa, N.J., pages 233-264). However, due to the lack of chromatographic selectivity and product yield, some (n-1)-mer impurities are still present in the full-length (i.e., n-mer) oligonucleotide product after the purification process. The (n-1) portion consists of the mixture of all possible single base deletion sequences relative to the n-mer parent oligonucleotide. Such (n-1) impurities can be classified as terminal deletion or internal deletion sequences, depending upon the position of the missing base (i.e., either at the 5' or 3' terminus or internally). When an oligonucleotide containing single base deletion sequence impurities is used as a drug (Crooke, *Hematologic Pathology*, 1995, 9, 59), the terminal deletion sequence impurities will bind to the same target mRNA as the full length sequence but with a slightly lower affinity. Thus, to some extent, such impurities can be considered as part of the active drug component, and are thus considered to be bioequivalents for purposes of the present invention.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. The compositions of the present invention may be formulated into any of many possible dosage forms such as, but not limited to, tablets, capsules, liquid syrups, soft gels, suppositories, and enemas.

Pharmaceutically acceptable organic or inorganic carrier substances suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously interact with the nucleic acid(s) of the formulation.

The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and formulations containing liposomes. While basically similar in nature these formulations vary in the components and the consistency of the final product. The know-how on the preparation of such compositions and formulations is generally known to those skilled in the pharmaceutical and formulation arts and may be applied to the formulation of the compositions of the present invention.

The compositions of the present invention may be prepared and formulated as emulsions. Emulsions are typically heterogenous systems of one liquid dispersed in another in the form of droplets usually exceeding 0.1 um in diameter. (Idson, in *Pharmaceutical Dosage Forms. Disperse Systems*, Vol. 1, Lieberman, Rieger and Banker, Eds., Marcel Dekker, Inc., New York, N.Y., 1988, p. 199; Rosoff, in *Pharmaceutical Dosage Forms: Disperse Systems*, Vol. 1, Lieberman, Rieger and Banker, Eds., Marcel Dekker, Inc., New York, N.Y., 1988, p. 245; Block, in *Pharmaceutical Dosage Forms: Disperse Systems*, Vol. 2, Lieberman, Rieger and Banker, Eds., Marcel Dekker, Inc., New York, N.Y., 1988, p. 335; Higuchi et al., in "Remington's Pharmaceutical Sciences," Mack Publishing Co., Easton, Pa., 1985, p. 301). Emulsions are often biphasic systems comprising of two immiscible liquid phases intimately mixed and dispersed with each other. In general, emulsions may be either water in oil (w/o) or of the oil in water (o/w) variety. When an aqueous phase is finely divided into and dispersed as minute droplets into a bulk oily phase the resulting composition is called a water in oil (w/o) emulsion. Alternatively, when an oily phase is finely divided into and dispersed as minute droplets into a bulk aqueous phase the resulting composition is called an oil in water (o/w) emulsion.

Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil in water in oil (o/w/o) and water in oil in water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms: Disperse Systems*, Vol. 1, Lieberman, Rieger and Banker, Eds., Marcel Dekker, Inc., New York, N.Y., 1988, p. 199).

Synthetic surfactants, also known as surface active agents, have found wide applicability in the formulation of emulsions and have been reviewed in the literature (Rieger, in *Pharmaceutical Dosage Forms: Disperse Systems*, Vol. 1, Lieberman, Rieger and Banker, Eds., Marcel Dekker, Inc., New York, N.Y., 1988, p. 285; Idson, in *Pharmaceutical Dosage Forms. Disperse Systems*, Vol. 1, Lieberman, Rieger and Banker, Eds., Marcel Dekker, Inc., New York, N.Y., 1988, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group into: nonionic, anionic, cationic and amphoteric (Rieger, in *Pharmaceutical Dosage Forms: Disperse Systems*, Vol. 1, Lieberman, Rieger and Banker, Eds., Marcel Dekker, Inc., New York, N.Y., 1988, p. 285).

Naturally occuring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms: Disperse Systems*, Vol. 1, Lieberman, Rieger and Banker, Eds., Marcel Dekker, Inc., New York, N.Y., 1988, p. 335; Idson, Id., p. 199).

Hydrophilic colloids or hydrocolloids include naturally occuring gums and synthetic polymers such as polysaccharides (for example, acacia, agar, alginic acid, carrageenan, guar gum, karaya gum, and tragacanth), cellulose derivatives (for example, carboxymethylc cellulose and carboxypropyl cellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscocity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms: Disperse Systems*, Vol. 1, Lieberman, Rieger and Banker, Eds., Marcel Dekker, Inc., New York, N.Y., 1988, p. 199). Emulsion formulations for oral delivery have been very widely used because of reasons of ease of formulation, efficacy from an absorption and bioavailability standpoint. (Rosoff, in *Pharmaceutical Dosage Forms: Disperse Systems*, Vol. 1, Lieberman, Rieger and Banker, Eds., Marcel Dekker, Inc., New York, N.Y., 1988, p. 245; Idson, Id., p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms: Disperse Systems*, Vol. 1, Lieberman, Rieger and Banker, Eds., Marcel Dekker, Inc., New York, N.Y., 1988, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs. Polymers and Aggregate Systems*, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in "Remington's Pharmaceutical Sciences," Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms: Disperse Systems*, Vol. 1, Lieberman, Rieger and Banker, Eds., Marcel Dekker, Inc., New York, N.Y., 1988, p. 245; Block, Id., p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. Further advantages are that liposomes obtained from natural phospholipids are biocompatible and biodegradable, liposomes can incorporate a wide range of water and lipid soluble drugs, liposomes can protect encapsulated drugs in their internal compartments from metabolism and degradation (Rosoff, in *Pharmaceutical Dosage Forms: Disperse Systems*, Vol. 1, Lieberman, Rieger and Banker, Eds., Marcel Dekker, Inc., New York, N.Y., 1988, p. 245). Important considerations in the preparation of liposome formulations are the lipid surface charge, vesicle size and the aqueous volume of the liposomes. Liposomes can be administered orally and in aerosols and topical applications.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms. Disperse Systems*, Vol. 1, Lieberman, Rieger and Banker, Eds., Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms: Disperse Systems*, Vol. 1, Lieberman, Rieger and Banker, Eds., Marcel Dekker, Inc., New York, N.Y., 1988, p. 285).

In one embodiment of the invention, a nucleic acid is administered via the rectal mode. In particular, compositions for rectal administration include solutions (enemas and suppositories) and emulsions. Rectal suppositories for adults are usually tapered at one or both ends and typically weigh about 2 g each, with infant rectal suppositories typically weighing about one-half as much, when the usual base, cocoa butter, is used (Block, Chapter 87 In. *Remington's Pharmaceutical Sciences*, 18th Ed., Gennaro, ed., Mack Publishing Co., Easton, Pa., 1990).

The use of absorption-promoting adjuvants is known in the art for the modification of the barrier function of the rectal membrane and has been reviewed (Nishihata and Rytting, *Advanced Drug Delivery Reviews*, 1997, 28, 205). Absorption-promoting adjuvants have shown promising effects on the performance of formulations of poorly absorbed drugs such as moderately large water-soluble drugs and peptides. Enamine derivatives of amino acids have exhibited absorption promoting properties but the mechanism by which they increase rectal absorption is unclear. Compounds such as chelating agents, and sulfhydryl depleters have been shown to increase the rectal absorption of drugs through the paracellular route as well as the transcellular route. Salicylate and its derivatives also increase absorption of drugs administered via the rectal route via both paracellular and transcellular paths. Fatty acids show properties similar to salicylates when enhancing rectal absorption of drugs. Lectin is also known to increase rectal absorption of drugs via induction of microvillus infusion.

In a preferred embodiment of the invention, one or more nucleic acids are administered via oral delivery.

Compositions for oral administration include powders or granules, suspensions or solutions in water or non-aqueous media, capsules, sachets, troches, tablets or SECs (soft elastic capsules or "caplets"). Thickeners, flavoring agents, diluents, emulsifiers, dispersing aids, carrier substances or binders may be desirably added to such formulations. A tablet may be made by compression or molding, optionally with one or more accessory ingredients. Compressed tablets may be prepared by compressing in a suitable machine, the active ingredients in a free-flowing form such as a powder or granules, optionally mixed with a binder (PVP or gums such as tragecanth, acacia, carrageenan), lubricant (e.g. stearates such as magnesium stearate), glidant (talc, colloidal silica dioxide), inert diluent, preservative, surface active or dispersing agent. Preferred binders/disintegrants include EMDEX (dextrate), PRECIROL (triglyceride), PEG, and AVICEL (cellulose). Molded tablets may be made by molding in a suitable machine a mixture of the powdered compound moistened with an inert liquid diluent. The tablets may optionally be coated or scored and may be formulated so as to provide slow or controlled release of the active ingredients therein.

The use of such formulations has the effect of delivering the nucleic acid to the alimentary canal for exposure to the mucosa thereof. Accordingly, the formulation can contain an enteric material effective in protecting the nucleic acid from pH extremes of the stomach, or in releasing the nucleic acid over time to optimize the delivery thereof to a particular mucosal site. Enteric materials for acid-resistant tablets, capsules and caplets are known in the art and typically include acetate phthalate, propylene glycol, sorbitan monoleate, cellulose acetate phthalate (CAP), cellulose acetate trimellitate and hydroxy propyl methyl cellulose phthalate (HPMCP). Enteric materials may be incorporated within the dosage form or may be a coating substantially covering the entire surface of tablets, capsules or caplets. Enteric materials may also be accompanied by plasticizers which impart flexible resiliency to the material for resisting fracturing, for example during tablet curing or aging. Plasticizers are known in the art and typically include diethyl phthalate (DEP), triacetin, dibutyl sebacate (DBS), dibutyl phthalate (DBP) and triethyl citrate (TEC).

Various methods for producing formulations for alimentary delivery are well known in the art. See, generally, Nairn, Chapter 83; Block, Chapter 87; Rudnic et al., Chapter 89; Porter, Chapter 90; and Longer et al., Chapter 91 In: *Remington's Pharmaceutical Sciences*, 18th Ed., Gennaro, ed., Mack Publishing Co., Easton, Pa., 1990. The compositions of this invention can be converted in a known manner into the customary formulations, such as tablets, coated tablets, pills, granules, capsules, aerosols, syrups, emulsions, suspensions and solutions, using inert, non-toxic, pharmaceutically suitable excipients or solvents. The therapeutically active compound should in each case be present here in a concentration of about 0.5% to about 95% by weight of the total mixture, that is to say in amounts which are sufficient to achieve the stated dosage range. Compositions may be formulated in a conventional manner using additional pharmaceutically acceptable carriers or excipients as appropriate. Thus, the composition may be prepared by conventional means with carriers or excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

Capsules used for oral delivery may include formulations that are well known in the art. Further, multicompartment hard capsules with control release properties as described by Digenis et al., U.S. Pat. No. 5,672,359, and water permeable capsules with a multi-stage drug delivery system as described by Amidon et al., U.S. Pat. No. 5,674,530 may also be used to formulate the compositions of the present invention.

The formulation of pharmaceutical compositions and their subsequent administration is believed to be within the skill of those in the art. Specific comments regarding the present invention are presented below.

In general, for therapeutic applications, a patient (i.e., an animal, including a human) having or predisposed to a disease or disorder is administered one or more nucleic acids, including oligonucleotides, in accordance with the invention in a pharmaceutically acceptable carrier in doses ranging from 0.01 ug to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. In the context of the invention, the term "treatment regimen" is meant to encompass therapeutic, palliative and prophylactic modalities. Following treatment, the patient is monitored for changes in his/her condition and for alleviation of the symptoms of the disorder or disease state. The dosage of the nucleic acid may either be increased if the patient does not respond significantly to current dosage levels, or the dose may be decreased if an alleviation of the symptoms of the disorder or disease state is observed, or if the disorder or disease state has been abated.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ values found to be effective in in vitro and in vivo animal models. In general, dosage is from 0.01 µg to 100 g per kg of body weight, and may be given once or more daily, weekly, monthly or yearly, or even once every 2 to 20 years. An optimal dosing schedule is used to deliver a therapeutically effective amount of the nucleic acid being administered via a particular mode of administration.

The term "therapeutically effective amount," for the purposes of the invention, refers to the amount of nucleic acid-containing formulation which is effective to achieve an intended purpose without undesirable side effects (such as toxicity, irritation or allergic response). Although individual needs may vary, determination of optimal ranges for effective amounts of formulations is within the skill of the art. Human doses can be extrapolated from animal studies (Katocs et al., Chapter 27 In: *Remington's Pharmaceutical Sciences,* 18th Ed., Gennaro, ed., Mack Publishing Co., Easton, Pa., 1990). Generally, the dosage required to provide an effective amount of a formulation, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: *Goodman & Gilman's The Pharmacological Basis of Therapeutics,* 9th Ed., Hardman et al., eds., McGraw-Hill, New York, N.Y., 1996).

Following successful treatment, it may be desirable to have the patient undergo maintenance therapy to prevent the recurrence of the disease state, wherein the nucleic acid is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

Formulations for non-parenteral administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic carrier substances suitable for non-parenteral administration which do not deleteriously react with nucleic acids can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously interact with the nucleic acid(s) of the formulation. Aqueous suspensions may contain substances which increase the viscosity of the suspension including, for example, sodium carboxymethylcellulose, sorbitol and/or dextran. The suspension may also contain stabilizers.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

A number of bioequivalents of oligonucleotides and other nucleic acids may also be employed in accordance with the present invention. The invention therefore, also encompasses oligonucleotide and nucleic acid equivalents such as, but not limited to, prodrugs of oligonucleotides and nucleic acids, deletion derivatives, conjugates of oligonucleotides, aptamers, and ribozymes.

The methods and compositions of the present invention also encompass the myriad deletion oligonucleotides, both internal and terminal deletion oligonucleotides, that are synthesized during the process of solid-phase manufacture of oligonucleotides for such deletion sequences are for all practical purposes bioequivalents. Synthetic RNA molecules and their derivatives that possess specific catalytic activities are known as ribozymes and are also considered bioequivalents of oligonucleotides for the purposes of the methods and compositions of the present invention. Also considered bioequivalents of oligonucleotides, for the purposes of the methods and compositions of the present invention, are peptide nucleic acids (PNAs) and aptamers (see, generally, Ellington et al., Nature, 1990, 346, 818; U.S. Pat. No. 5,523,389 (Ecker et al., Jun. 4, 1996)).

The name aptamer has been coined by Ellington and Szostak (Nature, 1990, 346, 818) for nucleic acid molecules that fit and therefore bind with significant specificity to nonnucleic acid ligands such as peptides, proteins and small molecules such as drugs and dyes. Because of these specific ligand binding properties, nucleic acids and oligonucleotides that may be classified as aptamers may be readily purified or isolated via affinity chromatography using columns that bear immobilized ligand. Aptamers may be nucleic acids that are relatively short to those that are as large as a few hundred nucleotides. For example, Ellington and Szostak have reported the discovery of RNA aptamers that are 155 nucleotides long and that bind dyes such as Cibacron Blue and Reactive Blue 4 (Ellington and Szostak, Nature, 1990, 346, 818) with very good selectivity. While RNA molecules were first referred to as aptamers, the term as used in the present invention refers to any nucleic acid or oligonucleotide that exhibits specific binding to small molecule ligands including, but not limited to, DNA, RNA, DNA derivatives and conjugates, RNA derivatives and conjugates, modified oligonucleotides, chimeric oligonucleotides, and gapmers.

The invention is drawn to the non-parenteral administration of a nucleic acid, such as an oligonucleotide, having biological activity, to an animal. By "having biological activity," it is meant that the nucleic acid functions to modulate the expression of one or more genes in an animal as reflected in either absolute function of the gene (such as ribozyme activity) or by production of proteins coded by such genes. In the context of this invention, "to modulate" means to either effect an increase (stimulate) or a decrease (inhibit) in the expression of a gene. Such modulation can be achieved by, for example, an antisense oligonucleotide by a variety of mechanisms known in the art, including but not limited to transcriptional arrest; effects on RNA processing (capping, polyadenylation and splicing) and transportation; enhancement or reduction of cellular degradation of the target nucleic acid; and translational arrest (Crooke et al., Exp. Opin. Ther. Patents, 1996, 6, 1).

In an animal other than a human, the compositions and methods of the invention can be used to study the function of one or more genes in the animal. For example, antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., Nature, 1993, 363, 260; Dean et al., Proc. Natl. Acad. Sci. U.S.A., 1994, 91, 11762; and Wahlestedt et al., Science, 1993, 259, 528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., Trends Pharmacol. Sci., 1994, 15, 250).

As stated, the compositions and methods of the invention are useful therapeutically, i.e., to provide therapeutic, palliative or prophylactic relief to an animal, including a human, having or suspected of having or of being susceptible to, a disease or disorder that is treatable in whole or in part with one or more nucleic acids. The term "disease or disorder" (1) includes any abnormal condition of an organism or part, especially as a consequence of infection, inherent weakness, environmental stress, that impairs normal physiological functioning; (2) excludes pregnancy per se but not autoimmune and other diseases associated with pregnancy; and (3) includes cancers and tumors. The term "having or suspected of having or of being susceptible to" indicates that the subject animal has been determined to be, or is suspected of being, at increased risk, relative to the general population of such animals, of developing a particular disease or disorder as herein defined. For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment, Chapter 5 In: Genetic Monitoring and Screening in the Workplace, OTA-BA-455, U.S. Government Printing Office, Washington, D.C., 1990, pages 75-99). The term "a disease or disorder that is treatable in whole or in part with one or more nucleic acids" refers to a disease or disorder, as herein defined, (1) the management, modulation or treatment thereof, and/or (2) therapeutic, palliative and/or prophylactic relief therefrom, can be provided via the administration of more nucleic acids. In a preferred embodiment, such a disease or disorder is treatable in whole or in part with an antisense oligonucleotide.

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Preparation of Oligonucleotides

A. General Synthetic Techniques: Oligonucleotides were synthesized on an automated DNA synthesizer using standard phosphoramidite chemistry with oxidation using iodine. Beta-cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1-1-dioxide in acetonitrile for the stepwise thiation of the phosphite linkages.

The synthesis of 2'-O-methyl-(2'-methoxy-)phosphorothioate oligonucleotides is according to the procedures set forth above substituting 2'-O-methyl b-cyanoethyldiisopropyl phosphoramidites (Chemgenes, Needham, Mass.) for standard phosphoramidites and increasing the wait cycle after the pulse delivery of tetrazole and base to 360 seconds.

Similarly, 2'-O-propyl-(a.k.a 2'-propoxy-)phosphorothioate oligonucleotides are prepared by slight modifications of this procedure and essentially according to procedures disclosed in U.S. patent application Ser. No. 08/383,666, filed Feb. 3, 1995, which is assigned to the same assignee as the instant application and which is incorporated by reference herein.

The 2'-fluoro-phosphorothioate oligonucleotides of the invention are synthesized using 5'-dimethoxytrityl-3'-phosphoramidites and prepared as disclosed in U.S. patent application Ser. No. 08/383,666, filed Feb. 3, 1995, and U.S. Pat. No. 5,459,255, which issued Oct. 8, 1996, both of which are assigned to the same assignee as the instant application and which are incorporated by reference herein. The 2'-fluoro-oligonucleotides are prepared using phosphoramidite chemistry and a slight modification of the standard DNA synthesis protocol (i.e., deprotection was effected using methanolic ammonia at room temperature).

PNA antisense analogs are prepared essentially as described in U.S. Pat. Nos. 5,539,082 and 5,539,083, both of which (1) issued Jul. 23, 1996, (2) are assigned to the same assignee as the instant application and (3) are incorporated by reference herein.

Oligonucleotides comprising 2,6-diaminopurine are prepared using compounds described in U.S. Pat. No. 5,506,351 which issued Apr. 9, 1996, and which is assigned to the same assignee as the instant application and incorporated by reference herein, and materials and methods described by Gaffney et al. (*Tetrahedron*, 1984, 40, 3), Chollet et al., (*Nucl. Acids Res.*, 1988, 16, 305) and Prosnyak et al. (*Genomics*, 1994, 21, 490). Oligonucleotides comprising 2,6-diaminopurine can also be prepared by enzymatic means (Bailly et al., *Proc. Natl. Acad. Sci. U.S.A.*, 1996, 93, 13623).

2'-Methoxyethoxy oligonucleotides of the invention are synthesized essentially according to the methods of Martin et al. (*Helv. Chim. Acta*, 1995, 78, 486).

B. Oligonucleotide Purification: After cleavage from the controlled pore glass (CPG) column (Applied Biosystems) and deblocking in concentrated ammonium hydroxide, at 55° C. for 18 hours, the oligonucleotides were purified by precipitation 2× from 0.5 M NaCl with 2.5 volumes of ethanol followed by further purification by reverse phase high liquid pressure chromatography (HPLC). Analytical gel electrophoresis was accomplished in 20% acrylamide, 8 M urea and 45 mM Tris-borate buffer (pH 7).

C. Oligonucleotide Labeling: Antisense oligonucleotides were labeled in order to detect the presence of and/or measure the quantity thereof in samples taken during the course of the in vivo pharmacokinetic studies described herein. Although radiolabeling by tritium exchange is one preferred means of labeling antisense oligonucleotides for such in vivo studies, a variety of other means are available for incorporating a variety of radiological, chemical or enzymatic labels into oligonucleotides and other nucleic acids.

1. Tritium Exchange: Essentially, the procedure of Graham et al. (*Nucleic Acids Research*, 1993, 21, 3737) was used to label oligonucleotides by tritium exchange. Specifically, about 24 mg of oligonucleotide was dissolved in a mixture of 200 µL of sodium phosphate buffer (pH 7.8), 400 µL of 0.1 mM EDTA (pH 8.3) and 200 µL of deionized water. The pH of the resulting mixture was measured and adjusted to pH 7.8 using 0.095 N NaOH. The mixture was lyophilized overnight in a 1.25 mL gasketed polypropylene vial. The oligonucleotide was dissolved in 8.25 µL of b-mercaptoethanol, which acts as a free radical scavenger (Graham et al., *Nucleic Acids Research*, 1993, 21, 3737), and 400 µL of tritiated $H_2O$ (5 Ci/gram). The tube was capped, placed in a 90 EC oil bath for 9 hours without stirring, and then briefly centrifuged to remove any condensate from the inside lid of the tube. (As an optional analytical step, two 10 µL aliquots (one for HPLC analysis, one for PAGE analysis) were removed from the reaction tube; each aliquot was added to a separate 1.5 mL standard microfuge tube containing 490 µL of 50 uM sodium phosphate buffer (pH 7.8).) The oligonucleotide mixture is then frozen in liquid nitrogen and transferred to a lyophilization apparatus wherein lyophilization was carried out under high vacuum, typically for 3 hours. The material was then resuspended in mL of double-distilled $H_2O$ and allowed to exchange for 1 hour at room temperature. After incubation, the mixture was again quick frozen and lyophilized overnight. (As an optional analytical step, about 1 mg of the oligonucleotide material is removed for HPLC analysis.) Three further lyophilizations were carried out, each with approximately 1 mL of double-distilled $H_2O$, to ensure the removal of any residual, unincorporated tritium. The final resuspended oligonucleotide solution is transferred to a clean polypropylene vial and assayed. The tritium labeled oligonucleotide is stored at about −70 EC.

2. Other Means of Labeling Nucleic Acids: As is well known in the art, a variety of means are available to label oligonucleotides and other nucleic acids and to separate unincorporated label from the labeled nucleic acid. For example, double-stranded nucleic acids can be radiolabeled by nick translation and primer extension, and a variety of nucleic acids, including oligonucleotides, can be terminally radiolabeled by the use of enzymes such as T4 polynucleotide kinase or terminal deoxynucleotidyl transferase (see, generally, Chapter 3 In: *Short Protocols in Molecular Biology*, 2d Ed., Ausubel et al., eds., John Wiley & Sons, New York, N.Y., pages 3-11 to 3-38; and Chapter 10 In: *Molecular Cloning. A Laboratory Manual*, 2d Ed., Sambrook et al., eds., pages 10.1 to 10.70). It is also well known in the art to label oligonucleotides and other nucleic acids with nonradioactive labels such as, for example, enzymes, fluorescent moieties and the like (see, for example, Beck, *Methods in Enzymology*, 1992, 216, 143; and Ruth, Chapter 6 In: *Protocols for Oligonucleotide Conjugates* (*Methods in Molecular Biology*, Volume 26) Agrawal, S., ed., Humana Press, Totowa, N.J., 1994, pages 167-185).

Example 2

Oligonucleotide Targets and Sequences

The present invention is drawn to compositions and formulations comprising oligonucleotides or nucleic acids and one or more mucosal penetration enhancers, and methods of using such formulations. In one embodiment, such formulations are used to study the function of one or more genes in an animal other than a human. In a preferred embodiment, oligonucleotides are formulated into a pharmaceutical composition intended for therapeutic delivery to an animal, including a human. The following tables list, as exemplars, some preferred oligonucleotides intended for local or systemic therapeutic delivery, as desired, that may be administered via nonparenteral means according to the compositions and methods of the invention. Such desired oligonucleotides include, but are not limited to, those which modulate the expression of cellular adhesion proteins (Table 1). Other oligonucleotides are designed to modulate the rate of cellular proliferation (Table 2), or to have biological or therapeutic activity against miscellaneous disorders (Table 3) and diseases resulting from eukaryotic pathogens (Table 4), retroviruses including HIV (human immunodeficiency virus; Table 5) and non-retroviral viruses (Table 6). Further details regarding these oligonucleotides are provided in the Sequence Listing.

TABLE 1

TARGET OLIGONUCLEOTIDES DESIGNED TO MODULATE CELLULAR ADHESION

| Cell Surface Target Protein | Commercial or Common Name (if any) of Oligonucleotide | Oligonucleotide Sequence SEQ ID NO(S): |
|---|---|---|
| ICAM-1 | ISIS 2302 | 1 |
| ICAM-1 | ISIS 1939 | 2 |
| ICAM-1 | GM1595 | 3 |
| VCAM-1 | ISIS 5847 | 4 |
| VCAM-1 | GM1535 | 5 |
| ELAM-1 | GM1515, GM1516, GM1517 | 6, 7, 8 |

TABLE 2

OLIGONUCLEOTIDES DESIGNED TO MODULATE THE RATE OF CELLULAR PROLIFERATION

| Molecular Target | Commercial or Common Name (if any) of Oligonucleotide | Oligonucleotide Sequence SEQ ID NO(S): |
|---|---|---|
| c-myb | MYB-AS | 9 |
| vascular endothelial growth factor (VEGF) | | 10, 11, 12 |
| bcl-2 | | 13, 14, 15 |
| Ha-ras | ISIS 2503 | 16 |
| MRP | ISIS 7597 | 17 |
| A-raf kinase | ISIS 9069 | 18 |
| c-raf kinase | ISIS 5132 | 19 |

TABLE 3

OLIGONUCLEOTIDES DESIGNED TO HAVE THERAPEUTIC ACTIVITY AGAINST MISCELLANEOUS DISORDERS

| Disorder | Commercial or Common Name (if any) of Oligonucleotide | Oligonucleotide Sequence SEQ ID NO(S): |
|---|---|---|
| Alzheimer's disease | | 20, 21 |
| Beta-thalassemia | 5'ss & 3'ss | 22, 23 |

TABLE 4

OLIGONUCLEOTIDES DESIGNED TO HAVE THERAPEUTIC ACTIVITY AGAINST EUKARYOTIC PATHOGENS

| Pathogen/Disease | Commercial or Common Name (if any) of Oligonucleotide | Oligonucleotide Sequence SEQ ID NO(S): |
|---|---|---|
| Plasmodium/malaria | PSI, PSII | 24, 25 |
| Schistosoma/bloodfluke infections | | 26 |

TABLE 5

OLIGONUCLEOTIDES DESIGNED TO HAVE THERAPEUTIC ACTIVITY AGAINST RETROVIRUSES, INCLUDING HIV

| Virus/Molecular Target | Commercial or Common Name (if any) of Oligonucleotide | Oligonucleotide Sequence SEQ ID NO(S): |
|---|---|---|
| HIV-1/gag | GEM 91 | 27 |
| HIV-1/gag | | 28, 29 |
| HIV | AR 177 | 30 |
| HIV/tat, vpr, rev, env, nef | | 31, 32 |
| HIV/pol, env, vir | | 33, 34 |
| HIV-1/tat, rev, env, nef | | 35, 36 |
| HIV/gp120 | ISIS 5320 | 37 |
| Hepatitis C virus | ISIS 6547 | 38 |

TABLE 6

OLIGONUCLEOTIDES DESIGNED TO HAVE THERAPEUTIC ACTIVITY AGAINST NON-RETROVIRAL VIRUSES

| Virus/Molecular Target | Commercial or Common Name (if any) of Oligonucleotide | Oligonucleotide Sequence SEQ ID NO(S): |
|---|---|---|
| influenza virus | | 39, 40 |
| Epstein-Barr Virus | | 41, 42 |
| Respiratory Syncytial Virus | | 43, 44 |
| cytomegalovirus (CMV) | GEM 132 | 45 |
| CMV | | 46, 47 |
| CMV | ISIS 2922 | 48 |

Additional oligonucleotides that may be formulated in the compositions of the invention include, for example, ribozymes, aptamers, molecular decoys, External Guide Sequences (EGSs) and peptide nucleic acids (PNAs).

Example 3

Evaluation of Formulations By In Situ Perfusion of Rat Ileum

The formulations of the invention may be evaluated as follows.

Methods: In order to evaluate the formulations, in situ perfusion of rat ileum is performed essentially according to the procedure of Komiya et al. (*Int. J. Pharmaceut.*, 1980, 4:249). Specifically, male Sprague Dawley rats weighing 250-300 g are used. After overnight fasting, the rats are anesthetized with 5% pentobarbital (50 mg/kg) by intraperitoneal injection. After a midline abdominal incision is made, the small intestine is taken out and ileum section located. An incision is made at each end of a 20 cm ileum segment. The ileum segment is laid out in a uniform multiple-S arrangement with 3 bends. The luminal contents of the section are flushed with buffer. A 10 cm piece of silicon rubber tubing is inserted into the intestinal lumen at each incision and ligated with 3-0 silk suture. The proximal end tubing is connected to a 30 mL syringe containing oligonucleotide solution. The formulation is perfused through the intestinal segment by using Sage model 365 syringe pump at 0.125 mL/min. The outflow solution is collected in a 2 mL centrifuge tube over 5 min intervals for 80 mins. At the end of perfusion study, an aliquot of 0.3 mL blood sample is collected from the portal vein.

The oligonucleotide concentration in the solution before and after passing through a 20 cm ileum segment is analyzed by high pressure liquid chromatography (HPLC) while the plasma samples are analyzed by capillary electrophoresis (CE). In most cases, tritium labeled ISIS 2302 is used as a tracer and the radioactivity of solution measured by a liquid scintillation counter. The amount of the drug absorbed from the ileum is calculated by dividing the concentration from the average of last six outflow samples (steady state) to that of the inflow sample.

Example 4

Evaluation of the Bioavailability of Oligonucleotide from Formulations Following In Vivo (Intrajejunum) Instillation In order to evaluate the absolute oral bioavailability of ISIS 2302 formulations containing various penetration enhancers, in vivo intrajejunum instillation was performed with the following formulations (Table 7).

TABLE 7

Intrajejunum Formulations 4a-4c
ISIS 2302

| Formulation No. | Concentration | Penetration Enhancer(s) | |
|---|---|---|---|
| 4a Solution | 20 mg/ml | CDCA<br>Caprate<br>Laurate | 20 mg/ml<br>40 mg/ml<br>40 mg/ml |
| 4b Solution | 20 mg/ml | UDCA<br>Caprate<br>Laurate | 20 mg/ml<br>40 mg/ml<br>40 mg/ml |
| 4c | 12 mg/ml | Microemulsion | |

Formulation 4a: First, 100 mg CDCA was transferred to a 5 ml volumetric flask containing about 3 ml of buffer. The flask was shaken until the CDCA was completely dissolved. Next, 200 mg sodium caprate and 200 mg sodium laurate were added to the solution, and the flask was shaken until all of the solid material was completely dissolved. Then, 0.5 ml of ISIS 2302 stock solution (200 mg/ml) was added to the solution. Finally, the volume of the solution was adjusted to 5 ml with buffer.

Formulation 4b: First, 200 mg sodium caprate and 200 mg sodium laurate were transferred to a 5 ml volumetric flask containing about 3 ml of buffer. Then, 100 mg of UDCA was added and the flask was shaken until the UDCA was completely dissolved. Then, 0.5 ml of ISIS 2302 stock solution (200 mg/ml) was added to the solution. Finally, the volume of the solution was adjusted to 5 ml with buffer.

Formulation 4c: A microemulsion of ISIS 2302 was prepared essentially according to the procedures of Panayiotis (*Pharm. Res.*, 1984, 11:1385). An aliquot of 0.6 ml of ISIS 2302 stock solution (200 mg/ml) was transferred to a 30 ml beaker containing 1.0 ml of Tween 80 (Sigma Chemical Company St. Louis, Mo.). Next, a mixture of 6.3 ml of Captex 355 (Abitec Corp., Janesville, Wis.) and 2.1 ml of Capmul MCM (Abitec Corp.) was added to the beaker. The resultant solution was stirred until a clear solution was formed.

Methods: Precannulated Sprague-Dawley rats weighing 250-300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). An aliquot of 1.0 mL drug solution was then injected via a 27 gauge needle. The intestine was put back to the body carefully. Muscle was then surgically closed and skin was clipped after injection. Three hundred μL of blood was collected from a cannula at each sampling time point. The rats were sacrificed in the $CO_2$ chamber 24 hours after dosing. Livers and kidneys were excised and stored at –80 EC until analysis. Radioactivity of plasma and tissue samples were measured. Liver and kidney were also analyzed for oligonucleotide content by capillary gel electrophoresis (CGE).

Results: The results of study are summarized in Table 8. No significant amount (i.e., ~0%) of ISIS 2302 (SEQ ID NO:1) was absorbed when a control solution (i.e., one lacking any penetration enhancers) was used. In contrast, when formulated as a solution containing a mixture of penetration enhancers (Formulations 4a and 4b) the absolute bioavailability of ISIS 2302 was in the range of 8 to 23% in the examined target organs (liver and kidneys). The AUC(0-3h) shows 10-13% bioavailability. When formulated as a microemulsion (Formulation 4c), in the absence of any penetration enhancers, the absolute bioavailability was surprisingly found to be 19-29% in the target organs (liver and kidneys). Formulation 4c provided an AUC(0-3h) showing about 13% bioavailability that is comparable to the bioavailability seen with Formulations 4a and 4b that used penetration enhancers in solution. However, it should be noted that the AUC(0-3h) comparison tends to underestimate the bioavailability, since the blood concentration from the intestinal instillation is much higher than that from i.v. injection at 3 hours after dosing.

TABLE 8

Percent Absolute Bioavailability (% i.v.) of ISIS 2302 Following Intrajejunum Instillation in Rats

| Formulation No. (Dose) | Liver[1] | Kidney[1] | AUC(0-3 h) (ug × h/mL)[2] |
|---|---|---|---|
| Formulation 4a (80 mg/kg) | 17.4 | 17.8 | 10.7 |
| Formulation 4b (80 mg/kg) | 8.8 | 23.0 | 13.5 |
| Formulation 4c (48 mg/kg) | 19.8 | 29.1 | 13.6 |

[1] According to the CGE analysis - total oligonucleotide.
[2] According to analysis by radioactivity. AUC(0-3 h) was calculated for all in vivo instillation studies because the results from radioactivity measurements are comparable to those from HPLC analyses for the first 3 hour plasma samples.

Example 5

Preparation of Microemulsion Formulations

In order to evaluate the bioavailability of oligonucleotide microemulsions the following microemulsion formulations of ISIS 2302 were prepared (Table 9)

TABLE 9

Microemulsion Formulations 5a and 5b
ISIS 2302

| Formulation No. | Concentration | Components | |
|---|---|---|---|
| 5a | 12 mg/ml | Captex 355<br>Capmul MCM<br>Tween 80 | 3 parts<br>1 part<br>0.5 part |
| 5b | 4 mg/ml | Captex 355<br>Capmul MCM<br>Tween 80 | 3 parts<br>1 part<br>0.04 part |

Formulation 5a: A microemulsion of ISIS 2302 was prepared essentially according to the procedures of Panayiotis (*Pharm. Res.*, 1984, 11: 1385). An aliquot of 0.6 ml of ISIS 2302 stock solution (200 mg/ml) was transferred to a 30 ml beaker containing 1.0 ml of Tween 80 (Sigma Chemical Company St. Louis, Mo.). Next, a mixture of 6.3 ml of Captex 355 (Abitec Corp., Janesville, Wis.) and 2.1 ml of Capmul MCM (Abitec Corp., Janesville, Wis.) was added to the beaker. The resultant solution was stirred until a clear solution was formed.

Formulation 5b: A water-in-oil microemulsion of ISIS 2302 was prepared essentially by adding the oil phase to the aqueous phase with adequate mixing. The aqueous phase was prepared by mixing 1 ml of a 100 mg/ml solution of ISIS 2302 and 1 ml of Tween 80 (Sigma Chemical Company St. Louis, Mo.). The oil phase was prepared by mixing 3 parts of Captex 355 (Abitec Corp., Janesville, Wis.) and 1 part of Capmul MCM (Abitec Corp., Janesville, Wis.). The oil phase was added to the aqueous phase with adequate stirring until the resultant mixture was a clear solution.

Example 6

Preparation of Water-in-Oil (W/O) Cream Formulations

In order to evaluate the bioavailability of oligonucleotide emulsions the water-in-oil cream formulations of ISIS 2302 described in Table 10 were prepared as follows.

Formulation 6a1: A water-in-oil cream formulation of ISIS 2302 was prepared by first preparing the two phases. A 2 ml aliquot of the ISIS 2302 stock solution (100 mg/ml) was mixed with 2 ml water in a 10 ml beaker and warmed to 70° C. A mixture of 1 gram of Grill 3 (Croda, U.S.), 3 ml Captex 355 (Abitec Corp., Janesville, Wis.) and 3 ml of Labrasol (Gattefosse, France) was prepared in a 30 ml beaker and this mixture was also warmed to 70° C. The aqueous solution of oligonucleotide was then poured slowly into the oil phase with vigorous mixing. Upon cooling to ambient temperature the desired water-in-oil cream formulation of oligonucleotide (~20 mg/mL) was obtained.

Formulation 6a2: A water-in-oil cream formulation of ISIS 2302 was prepared by first preparing the two phases. A 1.5 ml aliquot of the ISIS 2302 stock solution (200 mg/ml) was transferred to a 10 ml beaker and warmed to 70° C. In a 30 ml beaker were placed 0.5 gram of Grill 3 (Croda, U.S.), 1.5 ml Captex 355 (Abitec Corp., Janesville, Wis.), and 1.5 ml of Labrasol (Gattefosse, France) and this mixture also warmed to 70° C. The aqueous solution of oligonucleotide was then poured slowly into the oil phase with vigorous mixing. Upon cooling to ambient temperature the desired water-in-oil cream formulation oligonucleotide (~60 mg/mL) was obtained.

TABLE 10

Water-in-Oil Cream Formulations

6a1 (~20 mg/mL):
Aqueous Phase 2 ml ISIS 2302 solution (100 mg/ml)
2 mL water
Oil Phase 1 g. Grill 3 (Sorbitan Monostearate)
3 ml Captex 355
3 ml Labrasol
6a2 (~60 mg/mL)

TABLE 10-continued

Water-in-Oil Cream Formulations

Aqueous Phase 1.5 ml ISIS 2302 solution (200 mg/ml)
Oil Phase 0.5 g. Grill 3 (Sorbitan Monostearate)
1.5 ml Captex 355
1.5 ml Labrasol Example 7

Preparation of Oil-in-Water (O/W) Cream Formulations

In order to evaluate the bioavailability of oligonucleotide emulsions the following oil-in-water cream formulations of ISIS 2302 were prepared (Table 11).

TABLE 11

Oil-in-Water Cream Formulation 7a

Aqueous Phase 0.5 ml ISIS 2302 solution (200 mg/ml)
0.5 ml Tween 80
1.8 ml water
Oil Phase 100 mg. Grill 3 (Sorbitan Monostearate)
1 ml Captex 355
1 ml Labrasol Formulation 7a: An oil-in-water cream formulation of ISIS 2302 was prepared by first preparing the two phases. A 0.5 ml aliquot of the ISIS 2302 stock solution (200 mg/ml) was mixed with 0.5 ml of Tween 80 (Sigma Chemical Company St. Louis, Mo.) and 1.8 ml water in a 30 ml beaker and warmed to about 70° C. In a 10 ml beaker were placed 100 mg. of Grill 3 (Croda, U.S.), 1 ml Captex 355 (Abitec Corp., Janesville, Wis.), and 1 ml of Labrasol (Gattefosse, France) and this mixture also warmed to about 70° C. The oil phase was then poured into the aqueous solution of oligonucleotide with vigorous mixing. Upon cooling to ambient temperature the desired oil-in-water cream formulation was obtained.

Example 8

In Vivo Evaluation of Emulsion Formulations of ISIS 2302

(A) Following In Vivo Intrajejunum Instillation

In order to determine the ability of emulsion formulations to effectively deliver oligonucleotide drugs with adequate bioavailability the emulsion formulations of the invention were administered via intrajejunum instillation and the plasma concentrations of the oligonucleotide and AUC(0-3h) were measured.

Methods: Sprague-Dawley rats weighing 250-300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). An aliquot of 0.5 mL drug formulation was then injected via a 27 gauge needle. The intestine was put back into the body carefully. The incision portion was then covered with a wet gauze. 300 µL of blood was collected by a 27 gauge needle from the femoral vein at each sampling time point. The rats were sacrificed in a carbon dioxide chamber 3 hours after dosing. Plasma samples were analyzed by HPLC.

Formulations: A 20 mg/ml solution of ISIS 2302 was used as a control formulation. Water-in-oil cream formulations (Formulation 6a1 and 6a2) were used as the test formulation at two dosage levels—10 mg/rat (6a1) and 30 mg/rat (6a2).

Results: The results of study are summarized in Table 12. No significant amount (i.e., ~0%) of ISIS 2302 (SEQ ID NO:1) was absorbed when a control solution of the oligonucleotide was used. In contrast, when formulated as a water-in-oil cream (Formulation 6a1), the blood concentration of ISIS 2302 was found to reach a high of about 34 µg/ml (as determined by HPLC) within 0.5 h of dosing at 10 mg/rat. The concentration of total oligonucleotides, which includes n-1 oligo and related ISIS 2302 metabolites, was observed to be as high as about 36 µg/ml within 0.5 h of dosing. When the rats were dosed at 30 mg/animal (formulation 6a2) the blood concentration of ISIS 2302 was found to reach a high of about 64 µg/ml (and total oligonucleotides reached 81 µg/ml) within 0.5 h of dosing. The AUC(0-3h) of ISIS 2302 was determined to be 55 ug×h/mL from the 10 mg/rat dose and 81 ug×h/mL from the 30 mg/rat dosing.

Results: The results of study are summarized in Table 13. No significant amount (i.e., ~0%) of ISIS 2302 (SEQ ID NO:1) was absorbed when a control solution of the oligonucleotide was used. In contrast, when the oligonucleotide was administered rectally as a water-in-oil microemulsion (Formulation 5b) at 10 mg/rat significant absorption of the oligonucleotide occured as observed from blood levels of about 21 µg/mL within 0.5 h and an AUC(0-2h) of about 28 ug×h/mL.

When formulated as a water-in-oil cream (Formulation 6a1) the plasma concentration of ISIS 2302 was found to reach a high of about 34 µg/ml (as determined by HPLC) within 0.5-1.0 h of dosing at 10 mg/rat. The concentration of total oligonucleotides, which includes N-1 oligo and related ISIS 2302 metabolites was observed to be as high as about 45 µg/ml within 0.5-1.0 h of dosing. When the rats were dosed at 30 mg/animal (formulation 6a2) the plasma concentration of ISIS 2302 was found to reach a high of about 105 µg/ml (and total oligonucleotides reached 136 µg/ml) within 0.5 h of dosing. The AUC(0-3h) was determined to be 64 ug×h/mL from the 10 mg/rat dose and 143 ug×h/mL from the 30 mg/rat dosing. A similar increase in delivery of the oligonucleotide into the blood circulation was observed with the oil-in-water

TABLE 12

Blood Concentrations[1] and AUC(0-3 h) of ISIS 2302 After Intrajejunum Instillation in Rats

| Formulation No./Dose | Time (h.) | ISIS 2302 Blood Conc. (ug/ml) | Total Oligo Blood Conc. (ug/ml) | ISIS 2302 AUC(0-3 h) (ug · h/ml) | Total AUC(0-3 h) (ug · h/ml) |
|---|---|---|---|---|---|
| 6a1 | 0.5 | 33.73 | 35.98 | 55.24 | 50.64 |
|  | 1 | 29.53 | 29.11 |  |  |
| 10 mg/rat | 2 | 16.45 | 15.15 |  |  |
|  | 3 |  | 0.33 |  |  |
| 6a2 | 0.5 | 64.11 | 80.63 | 81.52 | 101.19 |
|  | 1 | 48.49 | 61.77 |  |  |
| 30 mg/rat | 2 | 17.67 | 21.28 |  |  |
|  | 3 | 6.89 | 6.70 |  |  |

[1]As determined by HPLC analysis.

(B) Following Rectal Administration

In order to determine the ability of emulsion formulations to effectively deliver oligonucleotide drugs with adequate bioavailability the emulsion formulations of the invention were administered via the rectum and the blood concentrations of the oligonucleotide and AUC(0-3h) were measured.

Methods: Sprague-Dawley rats weighing 250-300 g were used. After overnight fasting, the rats were anesthetized with 5% pentobarbital (50 mg/kg) by intraperitoneal injection. Test rats were first administered a cleansing enema and then dosed with a sample of the test formulation. A 0.5 ml formulation was applied via a 2 cm length catheter. The rat was lifted up by the bottom in a 15 degree angle to prevent the sample leakage during the experimental period. 300 µL of blood was collected by a 27 guage needle from the femoral vein at each sampling time point. The rats were sacrificed in a carbon dioxide chamber 3 hours after dosing. Plasma samples were analyzed by HPLC.

Formulations: A 20 mg/ml solution of ISIS 2302 was used as a control formulation. Three different emulsions of 2302 were evauated as test formulations: a water-in-oil microemulsion (Formulation 5b), a water-in-oil cream formulation (Formulations 6a1 and 6a2) and an oil-in-water cream formulation (Formulation 7a).

cream (Formulation 7a) when administered rectally at a dose of 10 mg/rat, but the AUC(0-3h) was lower than that observed with the water-in-oil cream.

Example 9

Determination of Bioavailability of Oligonucleotides following Intrajejunal and Rectal Administration of Formulations In order to determine the bioavailability of formulations of oligonucleotide drugs, two different modes of administration of oligonucleotide formulated in Formulation 6a1 were studied.

Methods:

Intrajejunal Instillation: Sprague-Dawley rats weighing 250-300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). An aliquot of 0.5 mL drug formulation was then injected via a 27 gauge needle. The intestine was put back into the body carefully.

TABLE 13

Plasma Concentrations[1] and AUC of ISIS 2302 After
Rectal Administration of Formulations to Rats

| Formulation No. & Dose | Time (h.) | ISIS 2302 plasma Conc. (µg/ml) | Total Oligo Plasma Conc. (µg/ml) | ISIS 2302 AUC (µg · h/ml) | Total AUC (µg · h/ml) |
|---|---|---|---|---|---|
| 5b | 0.5 | 21.31 | 29.00 | 27.95[2] | 40.85[2] |
|  | 1 | 19.00 | 25.05 |  |  |
| 10 mg/rat | 2 | 5.71 | 11.19 |  |  |
|  | 3 | N/A | N/A |  |  |
| 6a1 | 0.5 | 34.37 | 45.07 | 64.31[3] | 84.52[3] |
|  | 1 | 33.93 | 44.69 |  |  |
| 10 mg/rat | 2 | 20.84 | 27.42 |  |  |
|  | 3 | 10.26 | 13.37 |  |  |
| 6a2 | 0.5 | 105.84 | 136.49 | 115.85[3] | 143.29[3] |
|  | 1 | 71.64 | 98.49 |  |  |
| 30 mg/rat | 2 | 20.29 | 15.47 |  |  |
|  | 3 | 4.28 | 5.54 |  |  |
| 7a | 0.5 | 33.24 | 43.42 | 34.96[3] | 46.03[3] |
|  | 1 | 21.09 | 27.42 |  |  |
| 10 mg/rat | 2 | 4.87 | 6.74 |  |  |
|  | 3 | 3.61 | 4.89 |  |  |

[1]As determined by HPLC analysis.
[2]AUC(0-2 h).
[3]AUC(0-3 h).

Rectal Administration: Following a period of overnight fasting, the rats were anesthetized with 5% pentobarbital (50 mg/kg). Test rats were first administered a cleansing enema and then dosed with a sample of the test formulation. The enema formulation was applied via a 2 cm length catheter. The bottom part of rat was lifted up in a 15 degree angle to hold the solution.

In order to assess bioavailability of oligonucleotide, samples were processed and the amount of oligonucleotide present was assessed by HPLC analyses.

Results: The absolute bioavailability of ISIS 2302 (SEQ ID NO: 1) was determined following intrajejunal instillation in five Sprague-Daley rats and following rectal administration in seven rats. The results are shown in Table 14.

TABLE 14

Bioavailability of ISIS 2302 Following Intrajejunal
and Rectal Administration in Rats

| Route of Administration | Absolute Bioavailability |
|---|---|
| Intrajejunal | 20.3% (n = 5) |
| Rectal | 24.5% (n = 7) |

Example 10

Preparation of Emulsion Formulations Containing Penetration Enhancers

Various fatty acids, their salts and their derivatives act as penetration enhancers. These include, for example, oleic acid, a.k.a. cis-9-octadecenoic acid (or a pharmaceutically acceptable salt thereof, e.g., sodium oleate or potassium oleate); caprylic acid, a.k.a. n-octanoic acid (caprylate); capric acid, a.k.a. n-decanoic acid (caprate); lauric acid (laurate); acylcarnitines; acylcholines; and mono- and di-glycerides (Lee et al., *Critical Reviews in Therapeutic Drug Carrier Systems*, 1991, page 92).

Various natural bile salts, and their synthetic derivatives act as penetration enhancers. The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Goodman et al., eds., McGraw-Hill, New York, N.Y., 1996, pages 934-935). Bile salt derived penetration enhancers include, for example, cholic acid, cholalic acid or 3a,7a,12a-trihydroxy-5b-cholan-24-oic acid (or its pharmaceutically acceptable sodium salt); deoxycholic acid, desoxycholic acid, 5b-cholan-24-oic acid-3a,12a-diol, 7-deoxycholic acid or 3a,12a-dihydroxy-5b-cholan-24-oic acid (sodium deoxycholate); glycocholic acid, (N-[3a,7a,12a-trihydroxy-24-oxocholan-24-yl]glycine or 3a,7a,12a-trihydroxy-5b-cholan-24-oic acid N-[carboxymethyl]amide or sodium glycocholate); glycodeoxycholic acid, (5b-cholan-24-oic acid N-[carboxymethyl]amide-3a,12a-diol), 3a,12a-dihydroxy-5b-cholan-24-oic acid N-[carboxymethyl]amide, N-[3a,12a-dihydroxy-24-oxocholan-24-yl]glycine or glycodesoxycholic acid (sodium glycodeoxycholate); taurocholic acid, (5b-cholan-24-oic acid N-[2-sulfoethyl]amide-3a,7a,12a-triol), 3a,7a,12a-trihydroxy-5b-cholan-24-oic acid N-[2-sulfoethyl]amide or 2-[(3a,7a,12a-trihydroxy-24-oxo-5b-cholan-24-yl)amino]ethanesulfonic acid (sodium taurocholate); taurodeoxycholic acid, (3a,12a-dihydroxy-5b-cholan-2-oic acid N[2-sulfoethyl]amide or 2-[(3a,12a-dihydroxy-24-oxo-5b-cholan-24-yl)-amino]ethanesulfonic acid, or sodium taurodeoxycholate, or sodium taurodesoxycholate); chenodeoxycholic acid (chenodiol, chenodesoxycholic acid, 5b-cholanic acid-3a,7a-diol, 3a,7a-dihydroxy-5b-cholanic acid, or sodium chenodeoxycholate, or CDCA); ursodeoxycholic acid, (5b-cholan-24-oic acid-3a,7b-diol, 7b-hydroxylithocholic acid or 3a,7b-dihydroxy-5b-cholan-24-oic acid, or UDCA); sodium taurodihydro-fusidate (STDHF); and sodium glycodihydrofusidate (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782-783). Commercial sources of the penetration enhancers are listed in Table 15.

TABLE 15

Sources of Penetration Enhancers

| Compound Name | Abbreviation | Supplier |
|---|---|---|
| A. FATTY ACIDS AND DERIVATIVES | | |
| Capric acid, Na salt | caprate | Sigma[H] |
| Laurie acid, Na salt | laurate | Sigma |
| B. BILE SALTS AND DERIVATIVES | | |
| Cholic acid, Na salt | CA | Sigma |
| Glycholic acid, Na salt | GCA | Sigma |
| Glycodeoxycholic acid, Na Salt | GDCA | Sigma |
| Taurocholic acid, Na salt | TCA | Sigma |
| Taurodeoxycholic acid, Na salt | TDCA | Sigma |
| Chenodeoxycholic acid, Na salt | CDCA | Sigma |
| Ursodeoxycholic acid | UDCA | Aldrich[1] |

[H]Sigma, Sigma Chemical Company, St. Louis, MO.
[1]Aldrich, Aldrich Chemical Company, Milwaukee, WI.

In order to evaluate the ability of various penetration enhancers to enhance the oral delivery and/or mucosal penetration of oligonucleotides, and the bioavailability of oligonucleotides the following formulations were prepared (Table 16). Formulations 9a and 9c were prepared as emulsions of ISIS 2302 containing a combination of fatty acid and bile salt penetration enhancers. Formulations 9b and 9d were prepared such that the concentration of ISIS 2302 and the penetration enhancers remained the same as in Formulations 9a and 9c, respectively. However, formulations 9b and 9d are merely solution preparations and serve as comparison points for the emulsion formulations.

TABLE 16

ISIS 2302 Formulations Containing Penetration Enhancers (PE's) 9a-9d

| Formulation | Oil Phase | | Aqueous Phase | |
|---|---|---|---|---|
| 9a | Captex 355 | 1.25 ml | ISIS 2302 | 0.5 ml |
| | Labrasol | 1.25 ml | Mix. Of PE's | 1.0 ml |
| | Grill 3 | 0.5 g. | Water | 0.5 ml |
| | The aqueous phase contains 2% CDCA, 4% Sodium Laurate, and 4% Sodium Caprate | | | |
| 9b | Solution of ISIS 2302 (20 mg/ml) containing 2% CDCA, 4% Sodium Laurate, and 4% Sodium Caprate | | | |
| 9c | Captex 355 | 1.25 ml | ISIS 2302 | 0.5 ml |
| | Labrasol | 1.25 ml | Mix. Of PE's | 1.0 ml |
| | Grill 3 | 0.5 g. | Water | 0.5 ml |
| | The aqueous phase contains 2% UDCA, 4% Sodium Laurate, and 4% Sodium Caprate | | | |
| 9d | Solution of ISIS 2302 (20 mg/ml) containing 2% UDCA, 4% Sodium Laurate, and 4% Sodium Caprate | | | |

Note:
ISIS 2302 Stock Solution used was 200 mg/ml.

Formulation 9a: An emulsion formulation of ISIS 2302 was prepared by first preparing the two phases. A 0.5 ml aliquot of the ISIS 2302 stock solution (200 mg/ml) was mixed with 1.0 ml of the mixture of penetration enhancers (chenodeoxycholic acid sodium salt, sodium laurate and sodium caprate) and 0.5 ml water, and warmed to about 70° C. (aqueous phase). A separate mixture of 500 mg. of Grill 3 (Croda International Plc., East Yorkshire, U.K.), 1.25 ml Captex 355 (Abitec Corp., Janesville, Wis.), and 1.25 ml of Labrasol (Gattefosse Corp., Westwood, N.J.) was also prepared and warmed to about 70° C. (oil phase). The aqueous phase was then transferred to the oil phase with vigorous mixing to afford the desired emulsion concentration of 20 mg/ml ISIS 2302. The aqueous phase of emulsion contained 2% CDCA, 4% Sodium laurate, and 4% Sodium caprate.

Formulation 9b: Aliquots of the stock solution of ISIS 2302 (200 mg/ml) and mixture of penetration enhancers were mixed to afford a solution formulation comprising ISIS 2302 at a concentration of 20 mg/ml and a final concentration of 2% CDCA, 4% Sodium laurate and 4% Sodium caprate.

Formulation 9c: An emulsion formulation of ISIS 2302 was prepared by first preparing the two phases. A 0.5 ml aliquot of the ISIS 2302 stock solution (200 mg/ml) was mixed with 1.0 ml of the mixture of penetration enhancers (ursodeoxycholic acid sodium salt, sodium laurate and sodium caprate) and 0.5 ml water, and warmed to about 70° C. A separate mixture of 500 mg. of Grill 3 (Croda, U.S.), 1.25 ml Captex 355 (Abitec Corp., Janesville, Wis.), and 1.25 ml of Labrasol (Gattefosse, France) was also prepared and warmed to about 70° C. The aqueous phase was then transferred to the oil phase with vigorous mixing to afford the desired emulsion concentration of 20 mg/ml ISIS 2302. The aqueous phase of emulsion contained 2% UDCA, 4% Sodium laurate, and 4% Sodium caprate.

Formulation 9d: Aliquots of the stock solution of ISIS 2302 (200 mg/ml) and mixture of penetration enhancers were mixed to afford a solution formulation comprising ISIS 2302 at a concentration of 20 mg/ml and a final concentration of 2% UDCA, 4% Sodium laurate, and 4% Sodium caprate.

Example 11

Evaluation of Emulsion Formulations Containing Penetration Enhancers

In order to determine the ability of penetration enhancers to improve the absorption and delivery of oligonucleotide drugs the emulsion formulations of Example 9 were administered via intrajejunum instillation and the blood concentrations of the oligonucleotide and AUC(0-3h) were measured.

Methods: Sprague-Dawley rats weighing 250-300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). An aliquot of 0.5 mL drug formulation was then injected via a 27 gauge needle. The intestine was put back into the body carefully. The incision portion was covered with a wet gauze. 300 μL of blood was collected by a 27 gauge needle from the femoral vein at each sampling time point.

Formulations: Two emulsions (Formulations 9a and 9c) were evaluated at a dosage level of 10 mg/rat. The delivery of ISIS 2302 using these emulsions (Formulations 9a and 9c) formulated with a combination of penetration enhancers was compared to the performance of solutions (Formulations 9b and 9d, respectively) of ISIS 2302 that were formulated with the same combination and concentration of penetration enhancers.

Results: The results of study are summarized in Table 17. When a control solution of ISIS 2302 (SEQ ID NO: 1) was administered no significant amount of oligonucleotides was found to be absorbed. In contrast, when ISIS 2302 was formulated as a solution that contained a mixture of fatty acid and bile salts (Formulations 9b and 9d) a significant amount of oligonucleotide was found to be absorbed and present in the systemic circulation. The concentrations of oligonucleotide in plasma were found to be in the 42-73 μg/ml concentration range 30 mins after administration of Formulation 9b (at a dose of 10 mg/rat) which contains 2% CDCA. At the same time point 33-87 μg/ml of oligonucleotide was delivered into the blood circulation when Formulation 9d containing 2% UDCA was administered (at a dose of 10 mg/rat). The AUC(0-3h) was observed to be in the 48-58 ug×h/mL range from Formulation 9b and the 30-101 ug×h/mL range from administration of Formulation 9d.

Further increases in the amount of oligonucleotides delivered into systemic circulation were observed when the emulsions containing 2% bile salt together with 4% each of sodium laurate and sodium caprate were evaluated. Thus, Formulation 9a which incorporates the bile salt CDCA afforded 34-52 μg/ml concentrations of total oligonucleotide in the plasma within 30 minutes of administration and an AUC(0-3h) in the 63-151 ug×h/mL range. Likewise, Formulation 9c which incorporates the bile salt UDCA afforded 54-79 μg/ml concentrations of total oligonucleotide in the plasma within 30 minutes of administration and an AUC(0-3h) in the 84-127 μg.h/ml range.

Formulation 6a1 was prepared as an emulsion of ISIS 2302 in a mixture of labrasol, captex and Grill 3. Formulation 9a was also prepared as an emulsion that is similar to Formulation 6a1 with one difference in that CDCA and fatty acid penetration enhancers were incorporated into aqueous phase of Formulation 9a at the same concentrations as were present in Formulation 9b. Formulation 9c was likewise prepared as an emulsion that is similar to Formulation 6a1 with one difference in that UDCA and fatty acid penetration enhancers were incorporated into the aqueous phase of Formulation 9c at the same concentrations as were present in Formulation 9d.

All five formulations contained ISIS 2302 at a final concentration of 20 mg/ml.

Results: The results of absolute bioavailability of ISIS 2302 as determined in this study are summarized in Table 18.

TABLE 17

Plasma Concentrations[1] and AUC(0-3 h) of ISIS 2302 After Intrajejunum Instillation in Rats

| Formulation | Total #1 | Conc. Animal #2 | (mg/ml) #3 | Time (h.) | Formulation | Total #1 | Conc. Animal #2 | (mg/ml) #3 |
|---|---|---|---|---|---|---|---|---|
| 9a | 52.2 | 34.0 | 96.04 | 0.5 | 9b | 42.8 | 72.9 | 45.7 |
|  | 50.1 | 33.2 | 89.62 | 1 |  | 26.1 | 15.0 | 29.9 |
|  | 19.7 | 17.6 | 41.67 | 2 |  | 10.4 | 15.4 | 7.9 |
|  | 7.7 | 14.6 | 12.89 | 3 |  | 4.3 | 7.4 | 4.7 |
|  | 80.6 | 62.54 | 151.25 | AUC(0-3 h) |  | 48.13 | 57.7 | 49.8 |
| 9c | 54.8 | 53.7 | 78.6 | 0.5 | 9d | 33.3 | 87.3 |  |
|  | 53.4 | 56.6 | 84.6 | 1 |  | 17.1 | 63.0 |  |
|  | 18.0 | 17.4 | 32.0 | 2 |  | 4.2 | 18.6 |  |
|  | 10.6 | 5.1 | 5.0 | 3 |  | 0.6 | 5.1 |  |
|  | 83.9 | 82.54 | 127.44 | AUC(0-3 h) |  | 30.57 | 101.15 |  |

[1]As determined by HPLC analysis.

Example 11

Comparison of ISIS 2302 Bioavailability From Formulations Administered by Intrejenunal Instillation In order to determine the effectiveness of formulations the absolute bioavailability of oligonucleotide was assessed following intrajejunal instillation.

Methods: Sprague-Dawley rats weighing 250-300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). An aliquot of 0.5 mL drug formulation was then injected via a 27 gauge needle. The intestine was put back into the body carefully. The incision portion was covered with a wet gauze. 300 μL of blood was collected by a 27 gauge needle from the femoral vein at each sampling time point. The rats were sacrificed in a carbon dioxide chamber 3 hours after dosing. Plasma samples were analyzed by HPLC.

Formulations: Five formulations were evaluated. Two solution formulations were prepared. Formulation 9b was prepared by dissolving ISIS 2302 and a combination of CDCA and fatty acid penetration enhancers to the desired concentrations. Formulation 9d was prepared by dissolving ISIS 2302 and a combination of UDCA and fatty acid penetration enhancers to the desired concentrations.

TABLE 18

Absolute Bioavailability of ISIS 2302 Following Intrajejunal Installation in Rats

| Formulation | Composition | Absolute Bioavailability |
|---|---|---|
| 9b solution | ISIS 2302 + CDCA + Fatty acids | 14.6% (n = 5) |
| 9a emulsion | ISIS 2302 + CDCA + Fatty acids + Labrasol + Captex + Grill 3 | 27.7% (n = 3) |
| 9d solution | ISIS 2302 + UDCA + Fatty acids | 12.4% (n = 2) |
| 9c emulsion | ISIS 2302 + UDCA + Fatty acids + Labrasol + Captex + Grill 3 | 27.7% (n = 3) |
| 6a1 emulsion | ISIS 2302 + Labrasol + Captex + Grill 3 | 20.3% (n = 5) |

When a control solution of ISIS 2302 (SEQ ID NO:1) was administered, no significant amount of oligonucleotides was found to be absorbed. In contrast, when ISIS 2302 was formulated as a solution that contained a mixture of fatty acids and a bile salt (Formulations 9b and 9d), a significant amount of oligonucleotide was found to be absorbed and bioavailable in the systemic circulation. The absolute bioavailability of ISIS 2302 was found to be 14.6% from Formulation 9b (containing a mixture of CDCA and fatty acid penetration enhancers) and 12.4% from Formulation 9d (containing a mixture of UDCA and fatty acid penetration enhancers). The simple emulsion, Formulation 6a1, that is devoid of any penetration enhancers was also effective in making a significant portion of the ISIS 2302 oligonucleotide bioavailable (absolute bioavailability of 20.4%).

When formulated as emulsions that contained a combination of penetration enhancers, the bioavailability of ISIS 2302 was found to increase even further. Formulation 9a, which is an emulsion containing a combination of CDCA and fatty acid penetration enhancers, afforded an absolute bioavailability of ISIS 2302 to the tune of 27.7%. A similar bioavailability of the oligonucleotide was also found when emulsion Formulation 9c containing UDCA instead of CDCA, as in Formulation 9a, was evaluated.

Example 13

Preparation of Enema Formulations

To evaluate the delivery and mucosal penetration of oligonucleotides into the colon following rectal delivery, the following formulations were prepared (Table 19). Solution and emulsion formulations of ISIS 2302 (SEQ ID NO: 1) were prepared. Additives used in the formulations included saline, hydroxypropyl methyl cellulose (HPMC), carrageenan, Vitamin E a-tocopheryl polyethyelene glycol 1000 succinate (TPGS), Tween 80 and sorbitol.

TABLE 19

ISIS 2302 Formulations 12a-12f

| Formulation | Composition |
| --- | --- |
| 12a | ISIS 2302 in Saline |
| 12b | ISIS 2302 + 1.5% Hydroxypropyl Methyl Cellulose (HPMC) |
| 12c | ISIS 2302 + 1.0% Carrageenan + 2.5% Vitamin E a-Tocopheryl Polyethylene Glycol 1000 Succinate (TPGS) (Source: Eastman Chemical Company, NY) |
| 12d | ISIS 2302 in a w/o emulsion |
| 12e | ISIS 2302 + 0.5% Tween 80 + 0.75% HPMC |
| 12f | ISIS 2302 + 5% Sorbitol + 0.63% HPMC |
| 12g | ISIS 2302 in water |

Formulation 12a: A solution of ISIS 2302 was prepared by mixing 5 ml ISIS 2302 stock solution (100 mg/mL) with 95 ml sterile saline to have a final concentration of 5 mg/ml.

Formulation 12b: The solution was prepared by mixing 7.5 ml ISIS 2302 stock solution (100 mg/mL) with 142.5 ml hydroxypropyl methyl cellulose solution (HPMC) to have final concentrations of ISIS 2302 5 mg/ml and HPMC 15 mg/ml (1.5%). The HPMC solution was prepared by dissolving 2.25 g HPMC in 30 ml of 80° C. water and Q.S. to 142.5 mL with cold water.

Formulation 12c: The solution was prepared by mixing 7.5 ml ISIS 2302 stock solution (100 mg/ml) with 142.5 ml carrageenan/Vitamine E TPGS solution to have a final concentration of ISIS 2302 5 mg/ml, carrageenan 10 mg/ml (1%), and Vitamine E TPGS 25 mg/ml (2.5%). The carrageenan/Vitamine E TPGS solution was prepared by dissolving 1.5 g carrageenan and 3.75 g Vitamine E TPGS in 142.5 ml water. The solution was then heated to 60° C. to form a gel and cooled down to room temperature before the addition of ISIS 2302 stock solution.

Formulation 12d: A water-in-oil emulsion (w/o) of ISIS 2302 was prepared following the general methods in Examples 5 and 6. The emulsion containing 5 mg/ml of ISIS 2302.

Formulation 12e: The solution was prepared by mixing 6.0 ml ISIS 2302 stock solution (100 mg/ml) with 0.6 ml tween 80, and 113.4 ml HPMC solution to have final concentrations of ISIS 2302 5 mg/ml, tween 80 50 µl/ml (0.5%), and HPMC 7.5 mg/ml (0.75%). The HPMC solution was prepared by dissolving 0.9 g HPMC in 60 ml of 80° C. water and Q.S. to 113.4 ml with cool water.

Formulation 12f: The solution was prepared by mixing 6.0 ml ISIS 2302 stock solution (100 mg/ml) with 6 g sorbitol, and 108 ml HPMC solution to have final concentrations of ISIS 2302 5 mg/ml, sorbitol 50 mg/ml (5%), and HPMC 6.3 mg/ml (0.63%). The HPMC aolution was prepared by dissolving 0.75 g HPMC in 50 ml of 80° C. water and Q.S. to 108 ml with cool water.

Formulation 12g: A solution of ISIS 2302 was prepared by mixing 5 ml ISIS 2302 stock solution (100 mg/ml) with 95 ml water to have a final concentration of 5 mg/ml Example 14

Evaluation of Enema Formulations for Local Delivery of Oligonucleotide

Formulations of oligonucleotide were evaluated via rectal administration as enemas to laboratory beagle dogs.

Methods: Following a period of overnight fasting, test dogs were first administered a cleansing enema and then dosed with a sample of the test formulation. The enema formulation was applied via a Foley catheter and hold for a period of 1 h. In order to assess colonic tissue delivery and uptake of oligonucleotide, colon tissue biopsies were performed on the test animal, 3 h and 24 h after dosing. Tissue samples were processed and the amount of oligonucleotide present in the tissue assessed by capillary gel electrophoresis (CGE) and immunohistochemical (IHC) analyses.

Results: Seven formulations of ISIS 2302 (SEQ ID NO: 1) as prepared in Example 12 (Formulations 12a-12g) were administered to dogs via rectal enemas and the local distribution of ISIS 2302 in colonic tissue was determined by CGE and IHC at 3 h and 24 h following dosing. The results are shown in Table 20.

TABLE 20

Local Colonic Tissue Distribution of ISIS 2302 Following Rectal Enema in Dog

| Formulation | IHC | | CGE (µg/g) | |
| --- | --- | --- | --- | --- |
| | 3 h | 24 h | 3 h | 24 h |
| 12a | ++++ | – | 782 ± 664 | NA |
| 12b | ++++ | – | 660 ± 440 | 6.8 ± 5.0 |
| 12c | ++++ | – | 558 ± 212 | 2.5 ± 1.4 |
| 12d | ++++ | – | 224 ± 78 | 1.2 ± 0.7 |
| 12e | ++++ | – | 621 ± 368 | 6.0 ± 5.9 |
| 12f | ++++ | – | 417 ± 127 | 1.3 ± 0.5 |
| 12g | ++++ | – | 143 | NA |

Note:
"++++" indicates strong staining in IHC using a primary antibody to ISIS 2302; "–" indicates no significant staining compared to background levels.

Surprisingly, effective local colonic delivery of oligonucleotide was seen for a variety of formulations. Even oligonucleotide that was merely suspended in sterile saline (Formulation 12a) or water (Formulation 12g). The presence of HPMC, a protective colloid that is useful as a general dispersing and thickening excipient, did not hinder the localized delivery of oligonucleotide (Formulation 12b), nor did other additives, such as Carrageenan and TPGS (12c) Tween 80 (12e) or Sorbitol (12f).

The present disclosure thus provides for localized delivery of oligonucleotides and other small nucleic acids to the lower portion of the G.I. tract. Such delivery can be via means of an enema using a solution comprising an effective concentration of oligonucleotide. Alternatively, suppositories comprising oligonucleotides suspended in an agent that disperses its contents when exposed to the physical and/or chemical conditions of the colon. In addition to HMPC, a preferred dispersing agent for localized colconic delivery of oligonucleotides is cocoa butter.

Immunohistochemical (IHC) analyses were used to confirm and extend these results by determining the histopathology and cellular localization of rectally administered oligonucleotides in dogs. Biopsy samples were taken 10 to 20 centimeters from (i.e., approximately 18, 20, 21 and 22 cm from) the dorsal side of the colon and evaluated for the distribution of phosphorothioate oligodeoxynucleotide (P=S ODN) ISIS-2302 three hours after rectal administration. The biopsy samples were fixed in 10% neutral buffered formalin for 24 hours and transferred to 70% for storage. The tissues were embedded in paraffin and sectioned at 5 µm for immunohistochemical detection of P=S ODN. The affinity purified antibody used for this work, 2E1-B5, is a mouse IgG1 (Berkeley Antibody Company, Richmond, Calif.) which specifically recognizes P=S ODN.

Tissues were deparaffinized and pre-treated with proteinase K (Dako Corp., Carpenteria, Calif.) for 10 minutes at room temperature prior to incubation in the primary antibody. The antibody was detected with donkey anti mouse f(ab')2 IgG conjugated to horseradish peroxidase (Jackson Laboratories, West Grove, Pa.) and diaminobenzidene (DAB, Dako Corp.) was used as a substrate. All slides were stained on the Dako automated immuno-stainer.

Staining of the P=S ODN is seen in the nucleus of the surface epithelial layer at the tips of the colonic villi in all of the biopsies. The staining is strongest in the 20-22 cm samples and some staining is seen at the luminal surface of the epithelium, which is most likely associated with mucinous material in the colon.

Example 15

Bioavailability of Oligonucleotide Tablet Formulations: ISIS 2302 and ISIS 15839

In order to evaluate the potential for delivering oligonucleotides via various oral dosage forms, the following experiments were carried out.

A. Composition of and Preparation of Oral Dosage Formulations

The following oral dosage formulations of oligonucleotides were prepared as follows.

Oral Dosage Formulation a: ISIS 2302 with penetration enhancers (CDCA, SC, SL) and excipient precirol.

Oligonucleotide (ISIS 2302) was passed through a 60 mesh screen, 12.4 g of which was then mixed with 10 g sodium chenodeoxycholate (CDCA), 20 g of sodium caprate (SC), 20 g sodium laurate (SL) and 47.5 g precirol (WL 2155 ATO, prescreened on 60 mesh). The powder was then placed in a plastic bag, mixed thoroughly and then sifted through a 20 mesh screen. Powder blend was then compressed into tablets at slight weight overage using round flat-faced tooling. The resulting 1100" 50 mg tablets contained 124 mg oligonucleotide (as is by weight), 100 mg CDCA, 200 mg SL, 200 mg SC, and 476 mg precirol. Resultant tablets may be used as is (core tablets) or may be enteric film coated as described below under "Enteric Coating".

Oral Dosage Formulation b: ISIS 2302 with penetration enhancers (CDCA, SC, SL) and excipient (PEG).

Oligonucleotide (ISIS 2302) was passed through a 60 mesh screen and 9.3 g of which was mixed with 7.5 g sodium chenodeoxycholate (CDCA), 15 g of sodium caprate (SC), 15 g sodium laurate (SL) and 35.7 g polyethyleneglycol (20,000 mw PEG, prescreened 20 mesh). The powder was then placed in a plastic bag, mixed thoroughly and sifted through 20 mesh screen. Powder blend was then compressed into tablets at slight weight overage using round flat-faced tooling. The resulting 1100" 50 mg tablets contained 124 mg oligonucleotide (as is by weight), 100 mg CDCA, 200 mg SL, 200 mg SC, and 476 mg PEG. Resultant tablets may be used as is (core tablets) or may be enteric film coated as described below under "Enteric Coating".

Oral Dosage Formulation c: ISIS 15839 with penetration enhancers (CDCA, SC, SL) and excipient (PEG).

ISIS 15839 is a phosphorothioate isosequence "hemimer" derivative of ISIS 2302 having the structure 5'-GCC-CAA-GCT-GGC-ATC-CGT-CA-3' (SEQ ID NO:1), wherein emboldened "C" residues have 5-methylcytosine (m5c) bases and wherein the emboldened, double-underlined residues further comprise a 2'-methoxyethoxy modification (other residues are 2'-deoxy). ISIS 15839 is described in co-pending U.S. patent application Ser. No. 09/062,416, filed Apr. 17, 1998, hereby incorporated by reference.

ISIS 15839 was passed through a 60 mesh screen and 2.323 g of which was mixed with 2.0 g sodium chenodeoxycholate (CDCA), 4.0 g of sodium caprate (SC), 4.0 g sodium laurate (SL) and 9.523 g polyethyleneglycol (20,000 mw PEG, prescreened 20 mesh). The powder was then sifted through a 20 mesh screen and placed in a plastic bag and mixed thoroughly. Powder blend was then compressed into tablets at slight weight overage using 12 mm round tooling. The resulting 728.4" 10 mg tablets contained 77.44 mg oligonucleotide, 66.67 mg CDCA, 133.4 mg SL, 133.4 mg SC, and 317.5 mg PEG. Resultant tablets may be used as is (core tablets) may be enteric film coated as described below under "Enteric Coating".

Oral Dosage Formulation d: ISIS 2302 with penetration enhancers (CDCA, SC, SL) without excipient.

Oligonucleotide ISIS 2302 was passed through a 60 mesh screen and 3.72 g of which was mixed with 3 g sodium chenodeoxycholate (CDCA), 6 g of sodium caprate (SC) and 6 g sodium laurate (SL). The powder was sifted through a 20 mesh screen and placed in plastic bag and mixed thoroughly. This powder blend was then compressed into tablets at slight weight overage using 12 mm diameter tooling. The resulting 624" 10 mg tablets contained 124 mg oligonucleotide (as is by weight), 100 mg CDCA, 200 mg SL and 200 mg SC. Resultant tablets may be used as is (core tablets) or may be enteric film coated as described below under "Enteric Coating".

Enteric Coating (EC)

A cellulose acetate phthalate (CAP) enteric coating solution was prepared by slowly adding 7.0 g of CAP powder to 90.0 g stirred acetone. Before dissolving, 3.0 g diethyl phthalate was added and the solution covered with aluminum foil and continued to stir until dissolution was complete after approximately 30 minutes.

Core tablets were coated by hand by dipping into a stirred CAP solution using vacuum tubing to hold the tablet. As the coating dried the tablets were inverted and redipped to effect completion of a single coat over entire surface. This method may be repeated to impart an adequate enteric film coverage of 2 to 5% weight gain and, depending on tablet size and configuration, to allow for a uniform coat thickness and performance quality.

B. Evaluation of Oral Dosage Formulations

The tablet formulations were evaluated according to the following methods.

In Vitro: In order to evaluate the integrity of the enteric film coat, tablets were placed in 500 mL aqueous 0.1 N HCL acid solution (pH 1.5) using USP method II (paddles) at 150 rpm and 37° C. for up to 1 hour. Filtered samples were periodically taken and analyzed for presence of oligonucleotide as described below. Absence of oligonucleotide and visual inspection verified enteric coat integrity. Tablets were then placed into 500 mL of 0.2 M phosphate buffer solution, pH 6.5, to evaluate the rate at which oligonucleotides were released out of the tablets. Dissolution was monitored at regular time intervals by analyzing sample filtrate using UV light at 260 nm. This analysis was suitable for formulations devoid of interfering components (i.e., dissolved excipients capable of absorbing at 260 nm). Alternatively, samples may be analyzed by any of various separation methods (e.g., HPLC).

In Vivo: In order to measure the bioavailability of oligonucleotides from tablet formulations, tablets were administered orally (p.o.) to healthy beagle dogs of ~12 kg average weight at an approximate dose of 15 mg/kg. Blood samples were taken at regular time intervals and plasma harvested then subsequently analyzed for presence of oligonucleotide by either high pressure liquid chromatography (HPLC) for screening purposes or capillary gel electrophoresis (CGE) for purposes of confirmation and/or quantitation. Baseline pharmacokinetic intravenous (i.v.) data were obtained by administration of sterile drug solution (2 mg/kg) by slow i.v. push via antecubital vein followed by phlebotomies and analysis as described above.

Percent bioavailability was calculated from the resulting data according to the following formula % Bioavailability=$(AUC_{po}/D_o)/(AUC_{iv}/D_o) \times 100\%$, wherein $AUC_{po}$ is area under the plasma concentration curve for formulated oligonucleotide tablets administered orally, $AUC_{iv}$ is area under the plasma concentration curve for oligonucleotide administered as an i.v. solution (control), and $D_o$ is the respective dosages for these two regimens.

Results:

The results of the study are summarized in Table 21. As expected, enteric coated (EC) tablets had longer times of dissolution in acidic conditions (i.e., 4 minutes for ~50% dissolution for tablets lacking an enteric coating, from 7 to 14 minutes for EC tablets).

As indicated by the $C_{max}$ values, all of the oral dosage formulations tested can result in plasma concentrations of at least 1 ug/mL. Oral dosage formulation a, with or without an enteric coating, had $C_{max}$ values of 2.4 ug/mL and 2.0 mg/mL, respectively. A similar $C_{max}$ value was observed with enteric coated tablets of oral dosage formulation c. Oral dosage formulation b had the lowest $C_{max}$ value (1.2 ug/mL) when no enteric coating was provided but gave the highest $C_{max}$ value (3.3 mg/mL) when an enteric coating was used.

The % Bioavailability values generally followed the trend established by the $C_{max}$ values. For example, Oral dosage formulation b had the lowest % Bioavailability value when no enteric coating was provided but gave the highest % Bioavailability value when an enteric coating was used. As with $C_{max}$, the remaining oral dosage formulations had % Bioavailability values that are comparable to each other.

TABLE 21

In Vitro Dissolution of, and In Vivo Plasma Levels in Dogs Resulting from, Oral Dosage Formulations of ISIS 2302 and 15839

| Oral Dosage Formulation | $D_{50}$[1] (min) | $C_{max}$[2] (µg/mL) | % Bioavailability[3] |
|---|---|---|---|
| a core tablets | 4 | 2.4 | 2.0 |
| b core tablets | 4 | 1.2 | 0.9 |
| a with CAP EC[4] | 12 | 2.0 | 2.3 |
| b with CAP EC | 14 | 3.3 | 2.8 |
| c with CAP EC | 7 | 2.2 | 2.2 |

[1] $D_{50}$ = approximate time for 50% tablet dissolution.
[2] $C_{max}$ = maximum oligonucleotide concentration in plasma.
[3] Calculated as dose normalized AUC relative to i.v. AUC.
[4] CAP EC = cellulose acetate phthalate (CAP) enteric coating.

Example 16

Use of Other Animal Models to Evaluate Formulations

In order to further evaluate the bioavailability of the formulations of the invention, various animal models are used. For example, rectal formulations are tested in rats essentially according to the method of Aungst et al. (*Pharm. Res.*, 1988, 5:305) or in rabbits essentially according to the methods of Buur et al. (*J. Control Ret.*, 1990, 14.43) and Yamamoto et al. (*J. Pharmacol. Exper. Therapeutics*, 1992, 263:25).

The formulations of the invention are further evaluated in larger animals for optimization of the penetration enhancer (PE) systems in terms of, e.g., concentration and temporal effects on the absorption of oligonucleotides (ODN). Dogs will be "ported" with intestinal access catheters through which formulated drug formulations (solutions or suspensions) may be introduced into various areas of the gut. Target areas include the proximal jejunum and distal ilium or the iliocecal junction. These respective areas provide for ideal assessment of the systemic oligonucleotide bioavailability and for local tissue (e g., colonic) absorption. This latter objective is assessed on the basis of both tissue biopsy drug levels and/or inferred by the presence of drug in the plasma. In addition to ported dogs, naive dogs will be used for the assessment of formulations given by conventional routes, e.g., oral administration for oral dosage forms, rectal administration for enema or suppository formulations, etc. Dogs are dosed at 10 mg/kg of oligonucleotides, which are appropriately labeled as necessary, and blood samples are collected and evaluated for the presence and concentration of oligonucleotides. The absolute bioavailability is calculated and, if necessary, animals are sacrificed and tissue samples are collected and analyzed.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention. Also, it is intended that each of the patents and patent applications referenced above be incorporated by reference herein.

A further preferred oligonucleotide modification includes 2'-dimethylamino oxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference. Other preferred modifications include 2'-methoxy (2'-

O—CH$_3$), 2'-aminopropoxy (2'-OCH$_2$CH$_2$CH$_2$NH$_2$) and 2'-fluoro (2'-F). Similar modifications may also be made at other positions on the sugar group, particularly the 3' position of the sugar on the 3' terminal nucleotide or in 2'-5' linked oligonucleotides and the 5' position of 5' terminal nucleotide. The nucleosides of the oligonucleotides may also have sugar mimetics such as cyclobutyl moieties in place of the pentofuranosyl sugar.

Unsubstituted and substituted phosphodiester oligonucleotides are alternately synthesized on an automated DNA synthesizer (Applied Biosystems model 380B) using standard phosphoramidite chemistry with oxidation by iodine.

Phosphorothioates are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, hereby incorporated by reference.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Boranophosphate oligonucleotides are prepared as described in U.S. Pat. Nos. 5,130,302 and 5,177,198, both herein incorporated by reference.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and PO or PS linkages are prepared as described in U.S. Pat. Nos. 5,378,825; 5,386,023; 5,489,677; 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5.

They may also be prepared in accordance with U.S. Pat. Nos. 5,539,082; 5,700,922, and 5,719,262, herein incorporated by reference.

A further preferred oligonucleotide modification includes 2'-dimethylamino oxyethoxy, i.e., a O(CH$_2$)$_2$ON(CH$_3$)$_2$ group, also known as 2'-DMAOE, as described in co-owned U.S. patent application Ser. No. 09/016,520, filed on Jan. 30, 1998, the contents of which are herein incorporated by reference. Other preferred modifications include 2'-methoxy (2'-O—CH$_3$), 2'-aminopropoxy (2'-OCH$_2$CH$_2$CH$_2$NH$_2$) and 2'-fluoro (2'-F). Similar modifications may also be made at other positions on the sugar group, particularly the 3' position of the sugar on the 3' terminal nucleotide or in 2'-5' linked oligonucleotides and the 5' position of 5' terminal nucleotide. The nucleosides of the oligonucleotides may also have sugar mimetics such as cyclobutyl moieties in place of the pentofuranosyl sugar.

Unsubstituted and substituted phosphodiester oligonucleotides are alternately synthesized on an automated DNA synthesizer (Applied Biosystems model 380B) using standard phosphoramidite chemistry with oxidation by iodine.

Phosphorothioates are synthesized as per the phosphodiester oligonucleotides except the standard oxidation bottle was replaced by 0.2 M solution of 3H-1,2-benzodithiole-3-one 1,1-dioxide in acetonitrile for the stepwise thiation of the phosphite linkages. The thiation wait step was increased to 68 sec and was followed by the capping step. After cleavage from the CPG column and deblocking in concentrated ammonium hydroxide at 55° C. (18 hr), the oligonucleotides were purified by precipitating twice with 2.5 volumes of ethanol from a 0.5 M NaCl solution.

Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. Nos. 5,610,289 or 5,625,050, herein incorporated by reference.

Phosphoramidite oligonucleotides are prepared as described in U.S. Pat. No. 5,256,775 or U.S. Pat. No. 5,366,878, hereby incorporated by reference.

Alkylphosphonothioate oligonucleotides are prepared as described in published PCT applications PCT/US94/00902 and PCT/US93/06976 (published as WO 94/17093 and WO 94/02499, respectively).

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Boranophosphate oligonucleotides are prepared as described in U.S. Pat. Nos. 5,130,302 and 5,177,198, both herein incorporated by reference.

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and PO or PS linkages are prepared as described in U.S. Pat. Nos. 5,378,825; 5,386,023; 5,489,677; 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Peptide nucleic acids (PNAs) are prepared in accordance with any of the various procedures referred to in Peptide Nucleic Acids (PNA): Synthesis, Properties and Potential Applications, *Bioorganic & Medicinal Chemistry,* 1996, 4, 5. They may also be prepared in accordance with U.S. Pat. Nos. 5,539,082; 5,700,922, and 5,719,262, herein incorporated by reference.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

It is intended that each of the patents, applications, printed publications, and other published documents mentioned or referred to in this specification be herein incorporated by reference in their entirety.

What is claimed is:

1. An enema formulation comprising a solution or emulsion formulated for rectal administration as an enema, wherein said solution or emulsion comprises an oligonucleotide comprising SEQ ID NO: 1, and hydroxypropyl methyl cellulose (HPMC), without added penetration enhancer, wherein following the rectal administration of said solution or emulsion to an individual the oligonucleotide is taken up by at least one cell in the gastrointestinal tract, wherein said enema formulation comprising a solution or emulsion formulated for rectal administration as an enema is not a solid suppository, and wherein the amount of said HPMC is about 0.63% to about 1.5%.

2. The formulation of claim 1, wherein the oligonucleotide comprises ISIS 2302.

3. A method for rectal delivery of an oligonucleotide to at least one cell in a gastrointestinal tract of an individual comprising:
    identifying an individual in need of said oligonucleotide, and
    rectally administering to said individual an enema formulation comprising a solution or emulsion formulated for rectal administration as an enema, wherein said solution or emulsion comprises an oligonucleotide comprising SEQ ID NO: 1, and HPMC, without added penetration enhancer, wherein following the rectal administration of said solution or emulsion to said individual the oligonucleotide is taken up by at least one cell in the gastrointestinal tract, wherein said enema formulation comprising a solution or emulsion formulated for rectal administration as an enema is not a solid suppository, and wherein the amount of said HPMC is about 0.63% to about 1.5%.

4. The method of claim 3, wherein the oligonucleotide comprises ISIS 2302.

5. The method of claim 4 further comprising analyzing colon tissue for delivery of the oligonucleotide to at least one cell.

6. The method of claim 4 wherein the oligonucleotide is detectable in colon tissue at least three hours after rectal administration of the oligonucleotide.

7. The formulation of claim 1, wherein the amount of said HPMC is about 1.5%.

8. The method of claim 3, wherein the amount of said HPMC is about 1.5%.

9. The method of claim 3, wherein the oligonucleotide comprising SEQ ID NO: 1 is present at a concentration of 5 mg/ml.

* * * * *

SEQUENCE LISTING

```
<160> NUMBER OF SEQ ID NOS: 58

<210> SEQ ID NO 1
<211> LENGTH: 20
<212> TYPE: DNA
<213> ORGANISM: Artificial Sequence
<220> FEATURE:
<223> OTHER INFORMATION: antisense sequence

<400> SEQUENCE: 1
gcccaagctg gcatccgtca                                                  20

<210> SEQ ID NO 2
<211> LENGTH: 20
<212> TYPE: DNA
<213> ORGANISM: Artificial Sequence
<220> FEATURE:
<223> OTHER INFORMATION: antisense sequence

<400> SEQUENCE: 2
cccccaccac ttccctctc                                                   20

<210> SEQ ID NO 3
<211> LENGTH: 21
<212> TYPE: DNA
<213> ORGANISM: Artificial Sequence
<220> FEATURE:
<223> OTHER INFORMATION: antisense sequence

<400> SEQUENCE: 3
agccatagcg aggctgaggt t                                                21

<210> SEQ ID NO 4
<211> LENGTH: 20
<212> TYPE: DNA
<213> ORGANISM: Artificial Sequence
<220> FEATURE:
<223> OTHER INFORMATION: antisense sequence

<400> SEQUENCE: 4
aacatctccg taccatgcca                                                  20

<210> SEQ ID NO 5
<211> LENGTH: 21
<212> TYPE: DNA
<213> ORGANISM: Artificial Sequence
<220> FEATURE:
<223> OTHER INFORMATION: antisense sequence

<400> SEQUENCE: 5
cccaggcatt ttaagttgct g                                                21
```

<210> SEQ ID NO 6
<211> LENGTH: 21
<212> TYPE: DNA
<213> ORGANISM: Artificial Sequence
<220> FEATURE:
<223> OTHER INFORMATION: antisense sequence

<400> SEQUENCE: 6
gtttaaggca gcatcctaag a                                              21

<210> SEQ ID NO 7
<211> LENGTH: 21
<212> TYPE: DNA
<213> ORGANISM: Artificial Sequence
<220> FEATURE:
<223> OTHER INFORMATION: antisense sequence

<400> SEQUENCE: 7
tcacccaaag gtttaggctt g                                              21

<210> SEQ ID NO 8
<211> LENGTH: 21
<212> TYPE: DNA
<213> ORGANISM: Artificial Sequence
<220> FEATURE:
<223> OTHER INFORMATION: antisense sequence

<400> SEQUENCE: 8
gcaatcatga cttcaagagt t                                              21

<210> SEQ ID NO 9
<211> LENGTH: 18
<212> TYPE: DNA
<213> ORGANISM: Artificial Sequence
<220> FEATURE:
<223> OTHER INFORMATION: antisense sequence

<400> SEQUENCE: 9
gtgccggggt cttcgggc                                                  18

<210> SEQ ID NO 10
<211> LENGTH: 19
<212> TYPE: DNA
<213> ORGANISM: Artificial Sequence
<220> FEATURE:
<223> OTHER INFORMATION: antisense sequence

<400> SEQUENCE: 10
catggtttcg gagggcgtc                                                 19

<210> SEQ ID NO 11
<211> LENGTH: 20
<212> TYPE: DNA
<213> ORGANISM: Artificial Sequence
<220> FEATURE:
<223> OTHER INFORMATION: antisense sequence

<400> SEQUENCE: 11
tcgcgctccc tctctccggc                                                20

<210> SEQ ID NO 12
<211> LENGTH: 20
<212> TYPE: DNA
<213> ORGANISM: Artificial Sequence
<220> FEATURE:
<223> OTHER INFORMATION: antisense sequence

<400> SEQUENCE: 12
cacccaagag agcagaaagt                                              20

<210> SEQ ID NO 13
<211> LENGTH: 20
<212> TYPE: DNA
<213> ORGANISM: Artificial Sequence
<220> FEATURE:
<223> OTHER INFORMATION: antisense sequence

<400> SEQUENCE: 13
cccttcctac cgcgtgcgac                                              20

<210> SEQ ID NO 14
<211> LENGTH: 20
<212> TYPE: DNA
<213> ORGANISM: Artificial Sequence
<220> FEATURE:
<223> OTHER INFORMATION: antisense sequence

<400> SEQUENCE: 14
cctccgaccc atccacgtag                                              20

<210> SEQ ID NO 15
<211> LENGTH: 20
<212> TYPE: DNA
<213> ORGANISM: Artificial Sequence
<220> FEATURE:
<223> OTHER INFORMATION: antisense sequence

<400> SEQUENCE: 15
gttgacgtcc tacggaaaca                                              20

<210> SEQ ID NO 16
<211> LENGTH: 20
<212> TYPE: DNA
<213> ORGANISM: Artificial Sequence
<220> FEATURE:
<223> OTHER INFORMATION: antisense sequence

<400> SEQUENCE: 16
tccgtcatcg ctcctcaggg                                              20

<210> SEQ ID NO 17
<211> LENGTH: 20
<212> TYPE: DNA
<213> ORGANISM: Artificial Sequence
<220> FEATURE:
<223> OTHER INFORMATION: antisense sequence

<400> SEQUENCE: 17
tgctgttcgt gcccccgccg                                              20

<210> SEQ ID NO 18
<211> LENGTH: 20
<212> TYPE: DNA
<213> ORGANISM: Artificial Sequence
<220> FEATURE:
<223> OTHER INFORMATION: antisense sequence

<400> SEQUENCE: 18
ctaaggcaca aggcgggctg                                              20

<210> SEQ ID NO 19
<211> LENGTH: 20

```
<212> TYPE: DNA
<213> ORGANISM: Artificial Sequence
<220> FEATURE:
<223> OTHER INFORMATION: antisense sequence

<400> SEQUENCE: 19
tcccgcctgt gacatgcatt                                          20

<210> SEQ ID NO 20
<211> LENGTH: 25
<212> TYPE: DNA
<213> ORGANISM: Artificial Sequence
<220> FEATURE:
<223> OTHER INFORMATION: antisense sequence

<400> SEQUENCE: 20
cctctctgtt taaaacttta tccat                                    25

<210> SEQ ID NO 21
<211> LENGTH: 21
<212> TYPE: DNA
<213> ORGANISM: Artificial Sequence
<220> FEATURE:
<223> OTHER INFORMATION: antisense sequence

<400> SEQUENCE: 21
ttcatatcct gagtcatgtc g                                        21

<210> SEQ ID NO 22
<211> LENGTH: 18
<212> TYPE: DNA
<213> ORGANISM: Artificial Sequence
<220> FEATURE:
<223> OTHER INFORMATION: antisense sequence

<400> SEQUENCE: 22
gcuauuaccu uaacccag                                            18

<210> SEQ ID NO 23
<211> LENGTH: 17
<212> TYPE: DNA
<213> ORGANISM: Artificial Sequence
<220> FEATURE:
<223> OTHER INFORMATION: antisense sequence

<400> SEQUENCE: 23
cauuauugcc cugaaag                                             17

<210> SEQ ID NO 24
<211> LENGTH: 21
<212> TYPE: DNA
<213> ORGANISM: Artificial Sequence
<220> FEATURE:
<223> OTHER INFORMATION: antisense sequence

<400> SEQUENCE: 24 taaaagaat atgatcttca t                                         21

<210> SEQ ID NO 25
<211> LENGTH: 18
<212> TYPE: DNA
<213> ORGANISM: Artificial Sequence
<220> FEATURE:
<223> OTHER INFORMATION: antisense sequence

<400> SEQUENCE: 25
agcaactgag ccacctga                                            18
```

```
<210> SEQ ID NO 26
<211> LENGTH: 21
<212> TYPE: DNA
<213> ORGANISM: Artificial Sequence
<220> FEATURE:
<223> OTHER INFORMATION: antisense sequence

<400> SEQUENCE: 26
gccatagggg gcagggaagg c                                         21

<210> SEQ ID NO 27
<211> LENGTH: 25
<212> TYPE: DNA
<213> ORGANISM: Artificial Sequence
<220> FEATURE:
<223> OTHER INFORMATION: antisense sequence

<400> SEQUENCE: 27
ctctcgcacc catctctctc cttct                                     25

<210> SEQ ID NO 28
<211> LENGTH: 26
<212> TYPE: DNA
<213> ORGANISM: Artificial Sequence
<220> FEATURE:
<223> OTHER INFORMATION: antisense sequence

<400> SEQUENCE: 28
ctctcgcacc catctctctc cttcta                                    26

<210> SEQ ID NO 29
<211> LENGTH: 26
<212> TYPE: DNA
<213> ORGANISM: Artificial Sequence
<220> FEATURE:
<223> OTHER INFORMATION: antisense sequence

<400> SEQUENCE: 29
gctctcgcac ccatctctct ccttct                                    26

<210> SEQ ID NO 30
<211> LENGTH: 17
<212> TYPE: DNA
<213> ORGANISM: Artificial Sequence
<220> FEATURE:
<223> OTHER INFORMATION: antisense sequence

<400> SEQUENCE: 30
gtggtgggtg ggtgggt                                              17

<210> SEQ ID NO 31
<211> LENGTH: 26
<212> TYPE: DNA
<213> ORGANISM: Artificial Sequence
<220> FEATURE:
<223> OTHER INFORMATION: antisense sequence

<400> SEQUENCE: 31
gcctattctg ctatgtcgac acccaa                                    26

<210> SEQ ID NO 32
<211> LENGTH: 26
<212> TYPE: DNA
<213> ORGANISM: Artificial Sequence
<220> FEATURE:
<223> OTHER INFORMATION: antisense sequence
```

```
<400> SEQUENCE: 32
cttcgggcct gtcgggtccc ctcggg                                           26

<210> SEQ ID NO 33
<211> LENGTH: 26
<212> TYPE: DNA
<213> ORGANISM: Artificial Sequence
<220> FEATURE:
<223> OTHER INFORMATION: antisense sequence

<400> SEQUENCE: 33
gctggtgatc ctttccatcc ctgtgg                                           26

<210> SEQ ID NO 34
<211> LENGTH: 26
<212> TYPE: DNA
<213> ORGANISM: Artificial Sequence
<220> FEATURE:
<223> OTHER INFORMATION: antisense sequence

<400> SEQUENCE: 34
ctactactcc ttgactttgg ggattg                                           26

<210> SEQ ID NO 35
<211> LENGTH: 26
<212> TYPE: DNA
<213> ORGANISM: Artificial Sequence
<220> FEATURE:
<223> OTHER INFORMATION: antisense sequence

<400> SEQUENCE: 35
cttcgggcct gtcgggtccc ctcggg                                           26

<210> SEQ ID NO 36
<211> LENGTH: 26
<212> TYPE: DNA
<213> ORGANISM: Artificial Sequence
<220> FEATURE:
<223> OTHER INFORMATION: antisense sequence

<400> SEQUENCE: 36
cuucgggccu gucggguccc cucggg                                           26

<210> SEQ ID NO 37
<211> LENGTH: 8
<212> TYPE: DNA
<213> ORGANISM: Artificial Sequence
<220> FEATURE:
<223> OTHER INFORMATION: antisense sequence

<400> SEQUENCE: 37 ttggggtt                                                                8

<210> SEQ ID NO 38
<211> LENGTH: 20
<212> TYPE: DNA
<213> ORGANISM: Artificial Sequence
<220> FEATURE:
<223> OTHER INFORMATION: antisense sequence

<400> SEQUENCE: 38
gtgctcatgg tgcacggtct                                                  20

<210> SEQ ID NO 39
<211> LENGTH: 20
```

```
<212> TYPE: DNA
<213> ORGANISM: Artificial Sequence
<220> FEATURE:
<223> OTHER INFORMATION: antisense sequence

<400> SEQUENCE: 39
cattcaaatg gtttgcctgc                                                   20

<210> SEQ ID NO 40
<211> LENGTH: 20
<212> TYPE: DNA
<213> ORGANISM: Artificial Sequence
<220> FEATURE:
<223> OTHER INFORMATION: antisense sequence

<400> SEQUENCE: 40
gcaggcaaac catttgaatg                                                   20

<210> SEQ ID NO 41
<211> LENGTH: 25
<212> TYPE: DNA
<213> ORGANISM: Artificial Sequence
<220> FEATURE:
<223> OTHER INFORMATION: antisense sequence

<400> SEQUENCE: 41
tttgggtcca tcatcttcag caaag                                             25

<210> SEQ ID NO 42
<211> LENGTH: 20
<212> TYPE: DNA
<213> ORGANISM: Artificial Sequence
<220> FEATURE:
<223> OTHER INFORMATION: antisense sequence

<400> SEQUENCE: 42
catcatcttc agcaaagata                                                   20

<210> SEQ ID NO 43
<211> LENGTH: 20
<212> TYPE: DNA
<213> ORGANISM: Artificial Sequence
<220> FEATURE:
<223> OTHER INFORMATION: antisense sequence

<400> SEQUENCE: 43
acgcgaaaaa atgcgtacaa                                                   20

<210> SEQ ID NO 44
<211> LENGTH: 20
<212> TYPE: DNA
<213> ORGANISM: Artificial Sequence
<220> FEATURE:
<223> OTHER INFORMATION: antisense sequence

<400> SEQUENCE: 44
taaaccaaaa aaatggggca                                                   20

<210> SEQ ID NO 45
<211> LENGTH: 20
<212> TYPE: DNA
<213> ORGANISM: Artificial Sequence
<220> FEATURE:
<223> OTHER INFORMATION: antisense sequence

<400> SEQUENCE: 45
tggggcttac cttgcgaaca                                                   20
```

```
<210> SEQ ID NO 46
<211> LENGTH: 20
<212> TYPE: DNA
<213> ORGANISM: Artificial Sequence
<220> FEATURE:
<223> OTHER INFORMATION: antisense sequence

<400> SEQUENCE: 46
gacgtggggc ttaccttgcg                                               20

<210> SEQ ID NO 47
<211> LENGTH: 20
<212> TYPE: DNA
<213> ORGANISM: Artificial Sequence
<220> FEATURE:
<223> OTHER INFORMATION: antisense sequence

<400> SEQUENCE: 47
tcttcaacga cgtgggctt                                                20

<210> SEQ ID NO 48
<211> LENGTH: 21
<212> TYPE: DNA
<213> ORGANISM: Artificial Sequence
<220> FEATURE:
<223> OTHER INFORMATION: antisense sequence

<400> SEQUENCE: 48
gcgtttgctc ttcttcttgc g                                             21

<210> SEQ ID NO 49
<211> LENGTH: 20
<212> TYPE: DNA
<213> ORGANISM: Artificial Sequence
<220> FEATURE:
<223> OTHER INFORMATION: antisense sequence

<400> SEQUENCE: 49
gttctcgctg gtgagtttca                                               20

<210> SEQ ID NO 50
<211> LENGTH: 15
<212> TYPE: DNA
<213> ORGANISM: Artificial Sequence
<220> FEATURE:
<223> OTHER INFORMATION: antisense sequence

<400> SEQUENCE: 50
aacttgtgct tgctc                                                    15

<210> SEQ ID NO 51
<211> LENGTH: 20
<212> TYPE: DNA
<213> ORGANISM: Artificial Sequence
<220> FEATURE:
<223> OTHER INFORMATION: antisense sequence

<400> SEQUENCE: 51
gtgctcatgg tgcacggtct                                               20

<210> SEQ ID NO 52
<211> LENGTH: 20
<212> TYPE: DNA
<213> ORGANISM: Artificial Sequence
<220> FEATURE:
<223> OTHER INFORMATION: antisense sequence
```

```
<400> SEQUENCE: 52
gtgtgccaga caccctatct                                               20

<210> SEQ ID NO 53
<211> LENGTH: 20
<212> TYPE: DNA
<213> ORGANISM: Artificial Sequence
<220> FEATURE:
<223> OTHER INFORMATION: antisense sequence

<400> SEQUENCE: 53
gctgattaga gagaggtccc                                               20

<210> SEQ ID NO 54
<211> LENGTH: 20
<212> TYPE: DNA
<213> ORGANISM: Artificial Sequence
<220> FEATURE:
<223> OTHER INFORMATION: antisense sequence

<400> SEQUENCE: 54
ttgcttccat cttcctcgtc                                               20

<210> SEQ ID NO 55
<211> LENGTH: 20
<212> TYPE: DNA
<213> ORGANISM: Artificial Sequence
<220> FEATURE:
<223> OTHER INFORMATION: antisense sequence

<400> SEQUENCE: 55
gcccaagctg gcatccgtca                                               20

<210> SEQ ID NO 56
<211> LENGTH: 21
<212> TYPE: DNA
<213> ORGANISM: Artificial Sequence
<220> FEATURE:
<223> OTHER INFORMATION: antisense sequence

<400> SEQUENCE: 56
gcgtttgctc ttcttcttgc g                                             21

<210> SEQ ID NO 57
<211> LENGTH: 20
<212> TYPE: DNA
<213> ORGANISM: Artificial Sequence
<220> FEATURE:
<223> OTHER INFORMATION: antisense sequence

<400> SEQUENCE: 57
gttctcgctg gtgagtttca                                               20

<210> SEQ ID NO 58
<211> LENGTH: 20
<212> TYPE: DNA
<213> ORGANISM: Artificial Sequence
<220> FEATURE:
<223> OTHER INFORMATION: antisense sequence

<400> SEQUENCE: 58
gttctcgctg gtgagtttca                                               20
```